(12) United States Patent
Donaldson

(10) Patent No.: US 7,572,223 B2
(45) Date of Patent: *Aug. 11, 2009

(54) INTEGRATED PHYSIOLOGY AND IMAGING WORKSTATION

(75) Inventor: Brenda Donaldson, Harrison Township, MI (US)

(73) Assignee: General Electric Company, Schenectady, NY (US)

( * ) Notice: Subject to any disclaimer, the term of this patent is extended or adjusted under 35 U.S.C. 154(b) by 298 days.

This patent is subject to a terminal disclaimer.

(21) Appl. No.: 11/433,951

(22) Filed: May 15, 2006

(65) Prior Publication Data

US 2007/0016034 A1 Jan. 18, 2007

Related U.S. Application Data

(63) Continuation-in-part of application No. 11/182,473, filed on Jul. 15, 2005.

(51) Int. Cl.
*A61B 8/00* (2006.01)
*A61B 5/0402* (2006.01)

(52) U.S. Cl. ...................... 600/437; 600/523

(58) Field of Classification Search ............... 600/407, 600/410, 411, 437, 440–443, 453–457, 476–480, 600/509, 523
See application file for complete search history.

(56) References Cited

U.S. PATENT DOCUMENTS

| 5,203,337 | A | | 4/1993 | Feldman |
| 5,391,199 | A | | 2/1995 | Ben-Haim |
| 5,409,000 | A | | 4/1995 | Imran |
| 5,432,544 | A | * | 7/1995 | Ziarati ........................ 600/410 |
| 5,438,997 | A | | 8/1995 | Sieben et al. |
| 5,568,809 | A | | 10/1996 | Ben-Haim |
| 5,579,764 | A | | 12/1996 | Goldreyer |
| 5,588,432 | A | | 12/1996 | Crowley |
| 5,662,108 | A | | 9/1997 | Budd et al. |
| 5,687,737 | A | | 11/1997 | Branham |
| 5,713,946 | A | | 2/1998 | Ben-Haim |
| 5,771,895 | A | * | 6/1998 | Slager ........................ 600/462 |
| 5,840,031 | A | | 11/1998 | Crowley |

(Continued)

FOREIGN PATENT DOCUMENTS

DE 10340546 A1 3/2005

(Continued)

*Primary Examiner*—Eric F Winakur
(74) *Attorney, Agent, or Firm*—Dean Small; The Small Patent Law Group

(57) ABSTRACT

A physiology workstation includes a communications interface conveying physiology signals and ultrasound data representative of a region of interest. The ultrasound data is obtained by an ultrasound device in real-time during a procedure. Also includes is a physiology processing unit, an ultrasound processing unit, and a display unit displaying the physiology signals and the ultrasound images, the physiology signals and ultrasound signals being presented jointly to a user in real-time during the procedure being carried out on the subject. The display unit includes at least one monitor co-displaying the physiology signals and ultrasound images in adjacent windows on a single display. The physiology processing unit, ultrasound processing unit and display unit are located in a control room divided from a procedure room. The communications interface extends between the procedure and control rooms and the physiology processing unit is configured to remotely control the ultrasound system via the communications interface.

16 Claims, 15 Drawing Sheets

U.S. PATENT DOCUMENTS

| | | | |
|---|---|---|---|
| 6,019,725 A | 2/2000 | Vesely et al. | |
| 6,086,532 A | 7/2000 | Panescu et al. | |
| 6,102,863 A | 8/2000 | Pflugraph et al. | |
| 6,168,565 B1 | 1/2001 | Napolitano | |
| 6,200,269 B1 | 3/2001 | Lin et al. | |
| 6,216,027 B1 | 4/2001 | Willis et al. | |
| 6,246,898 B1 | 6/2001 | Vesely et al. | |
| 6,325,759 B1 * | 12/2001 | Pelissier | 600/443 |
| 6,389,311 B1 * | 5/2002 | Whayne et al. | 600/523 |
| 6,413,219 B1 | 7/2002 | Avila et al. | |
| 6,447,450 B1 | 9/2002 | Olstad | |
| 6,505,063 B2 | 1/2003 | Van Den Brink et al. | |
| 6,537,217 B1 | 3/2003 | Bjaerum et al. | |
| 6,650,927 B1 | 11/2003 | Kiedar | |
| 6,679,847 B1 | 1/2004 | Robinson et al. | |
| 6,705,992 B2 * | 3/2004 | Gatzke | 600/437 |
| 6,728,562 B1 | 4/2004 | Budd et al. | |
| 6,950,689 B1 | 9/2005 | Willis et al. | |
| 7,263,397 B2 | 8/2007 | Hauck et al. | |
| 7,285,117 B2 | 10/2007 | Krueger et al. | |
| 7,314,446 B2 | 1/2008 | Byrd et al. | |
| 7,485,115 B2 | 2/2009 | Nakamura | |
| 2003/0045795 A1 | 3/2003 | Bjaerum et al. | |
| 2003/0074011 A1 | 4/2003 | Gilboa et al. | |
| 2003/0120318 A1 | 6/2003 | Hauck | |
| 2003/0163045 A1 | 8/2003 | Gatzke | |
| 2003/0176778 A1 | 9/2003 | Messing et al. | |
| 2004/0097806 A1 | 5/2004 | Hunter et al. | |
| 2004/0080336 A1 | 7/2004 | Byrd et al. | |
| 2004/0127798 A1 | 7/2004 | Dala-Krishna et al. | |
| 2004/0147842 A1 | 7/2004 | Desmarais | |
| 2004/0152974 A1 | 8/2004 | Solomon | |
| 2004/0249259 A1 | 12/2004 | Heimdal et al. | |
| 2005/0080336 A1 | 4/2005 | Byrd et al. | |
| 2005/0090745 A1 * | 4/2005 | Steen | 600/447 |
| 2005/0096543 A1 | 5/2005 | Jackson et al. | |
| 2005/0131473 A1 | 6/2005 | Gordon et al. | |
| 2005/0171428 A1 | 8/2005 | Fichtinger et al. | |
| 2005/0203375 A1 | 9/2005 | Willis et al. | |
| 2006/0182320 A1 | 8/2006 | Peszynski | |
| 2006/0184016 A1 | 8/2006 | Glossop | |
| 2006/0229594 A1 | 10/2006 | Francischelli et al. | |
| 2006/0253030 A1 | 11/2006 | Altmann et al. | |
| 2006/0253031 A1 | 11/2006 | Altmann et al. | |
| 2006/0253032 A1 | 11/2006 | Altmann et al. | |
| 2007/0130287 A1 | 6/2007 | Kumar et al. | |
| 2007/0287902 A1 | 12/2007 | Fuimaono et al. | |
| 2008/177994 A1 | 7/2008 | Mayer | |

FOREIGN PATENT DOCUMENTS

| | | |
|---|---|---|
| EP | 1637070 A | 3/2005 |
| WO | WO 92/19157 | 11/1992 |
| WO | WO 01/20552 A1 | 3/2001 |

* cited by examiner

INTEGRATED PHYSIOLOGY AND IMAGING WORKSTATION

CROSS-REFERENCE TO RELATED APPLICATIONS

This application is a continuation-in-part of U.S. patent application Ser. No. 11/182,473, filed Jul. 15, 2005, entitled "INTEGRATED PHYSIOLOGY AND IMAGING WORKSTATION", which is hereby incorporated by reference in its entirety.

BACKGROUND OF THE INVENTION

Embodiments of the present invention generally relate to physiology and imaging workstations, and more particularly to integrating various physiology and imaging features and functionality into a single workstation.

Today, physiology workstations are used in catheter labs, hemodynamic (HD) labs and electrophysiology (EP) labs to conduct various tests and procedures. Sometimes, the laboratory is organized into a procedure room, a control room and a remote monitoring room. Alternatively, there may not be a separate control or remote monitoring room. Instead, a sterile area where the patient lies is in the center of the room, and located in another area of the same room are the EP system and HD system, stimulator, etc. When available, the control and remote monitoring rooms are isolated from the sterile environment of the procedure room and are shielded from the x-rays generated in the procedure room by certain types of imaging equipment, such as fluoroscopy, magnetic resonance (MR) or computed tomographic (CT) imaging equipment. Presently, physiology workstations located in either the procedure, control or monitoring rooms are attached through cables to sensors, catheters, and instruments related only to the study. For example, conventional workstations are directly attached to surface ECG leads, intercardiac leads provided on a catheter, pressure sensors provided on a catheter and the like. The EP workstation is also directly attached to a stimulator that induces stimulus signals through a pacing tip on the catheter, such as to induce pacing to the heart.

Presently, the physiology workstation operates entirely separate and independent from imaging systems provided, such as an ultrasound workstation. The ultrasound workstation is a stand-alone system positioned in the procedure room proximate the patient and is controlled and operated by the physician or designated operator. The ultrasound system is attached to an ultrasound catheter or a surface probe that obtains ultrasound images. The ultrasound system may be attached to various probes including transthoracic, transesophageal, intravascular or intracardiac. The ultrasound system is directly attached to a second set of surface ECG leads, separated and distinct from the surface ECG leads connected to the EP workstation. The ultrasound images are displayed on a dedicated ultrasound monitor positioned directly on the stand-alone ultrasound system in the procedure room. The ultrasound monitor in the procedure room is separate and distinct from the monitors in the control and remote monitoring rooms. The ultrasound system has a separate user interface dedicated and specific to ultrasound features and functionality. The ultrasound system also includes entirely independent and dedicated processing hardware and software, memory and the like. Thus, today, EP and HD studies are performed utilizing a stand-alone ultrasound system that is separate and distinct from the electrophysiology workstation.

Conventional EP and HD workstations and ultrasound systems suffer from various disadvantages, that are addressed by various embodiments of the present invention.

BRIEF SUMMARY OF THE INVENTION

Therefore, in one aspect of the present invention, there is provided a physiology workstation configuration that includes a communications interface conveying physiology signals derived from a subject and ultrasound data representative of a region of interest of the subject, the ultrasound data being obtained by an ultrasound device in real-time during a procedure carried out on the subject. The physiology workstation also includes a physiology processing unit receiving and processing the physiology signals, an ultrasound processing unit receiving and processing the ultrasound data to generate ultrasound images, the physiology processing unit combining the physiology signals with the ultrasound images from the ultrasound processing unit; and a display unit displaying the physiology signals and the ultrasound images, the physiology signals and ultrasound signals being presented jointly to a user in real-time during the procedure being carried out on the subject. The display unit includes at least one monitor, the monitor co-displaying the physiology signals and ultrasound images in adjacent windows on a single display. Also, the physiology processing unit, ultrasound processing unit and display unit are located in a control room that is divided from a procedure room where the subject is located, the communications interface extending between the procedure and control rooms and the physiology processing unit configured to remotely control the ultrasound system via the communications interface.

Another aspect of the present invention is a physiology system that includes EP leads configured to be attached to a subject located in a procedure room, an ultrasound system for obtaining ultrasound images of a region of interest of the subject, and a physiology processing unit communicating with the physiology leads and ultrasound system, the physiology processing unit receiving and processing physiology signals from the physiology leads and ultrasound images. The system also includes a display unit, joined to the physiology processing unit, displaying the physiology signals, and an ultrasound remote interface, joined to the physiology processing unit, for entering at least one of ultrasound control parameters and ultrasound modes. The ultrasound system is configured to adjust operation based on at least one of ultrasound control parameters and the ultrasound modes entered at the physiology processing unit. The ultrasound remote interface includes a secondary U/S keyboard mouse or soft key functions, or a combination thereof, wherein the U/S keyboard, mouse, or soft keys are located proximate the display unit, the ultrasound system further having a primary U/S keyboard.

Yet another aspect of the present invention is a physiology workstation that has a communications interface conveying physiology signals derived from a subject and ultrasound data representative of a region of interest of the subject, wherein the ultrasound data is obtained by an ultrasound device in real-time during a procedure carried out on the subject, a physiology processing unit receiving and processing the physiology signals, and an ultrasound processing unit receiving and processing the ultrasound data to generate ultrasound images, the physiology processing unit combining the physiology signals with the ultrasound images from the ultrasound processing unit. The workstation also includes a display unit displaying the physiology signals and the ultrasound images, the physiology signals and ultrasound signals being presented jointly to a user in real-time during the procedure being carried out on the subject. The display unit includes at least one monitor, the monitor co-displaying the physiology signals and ultrasound images in adjacent windows on a single display. Also provided is an ultrasound device connecting to one of various devices: an intravascular ultrasound catheter, an intracardiac echo catheter, a transthoracic probe, or a transesophageal probe.

DETAILED DESCRIPTION OF THE INVENTION

Figure 1:
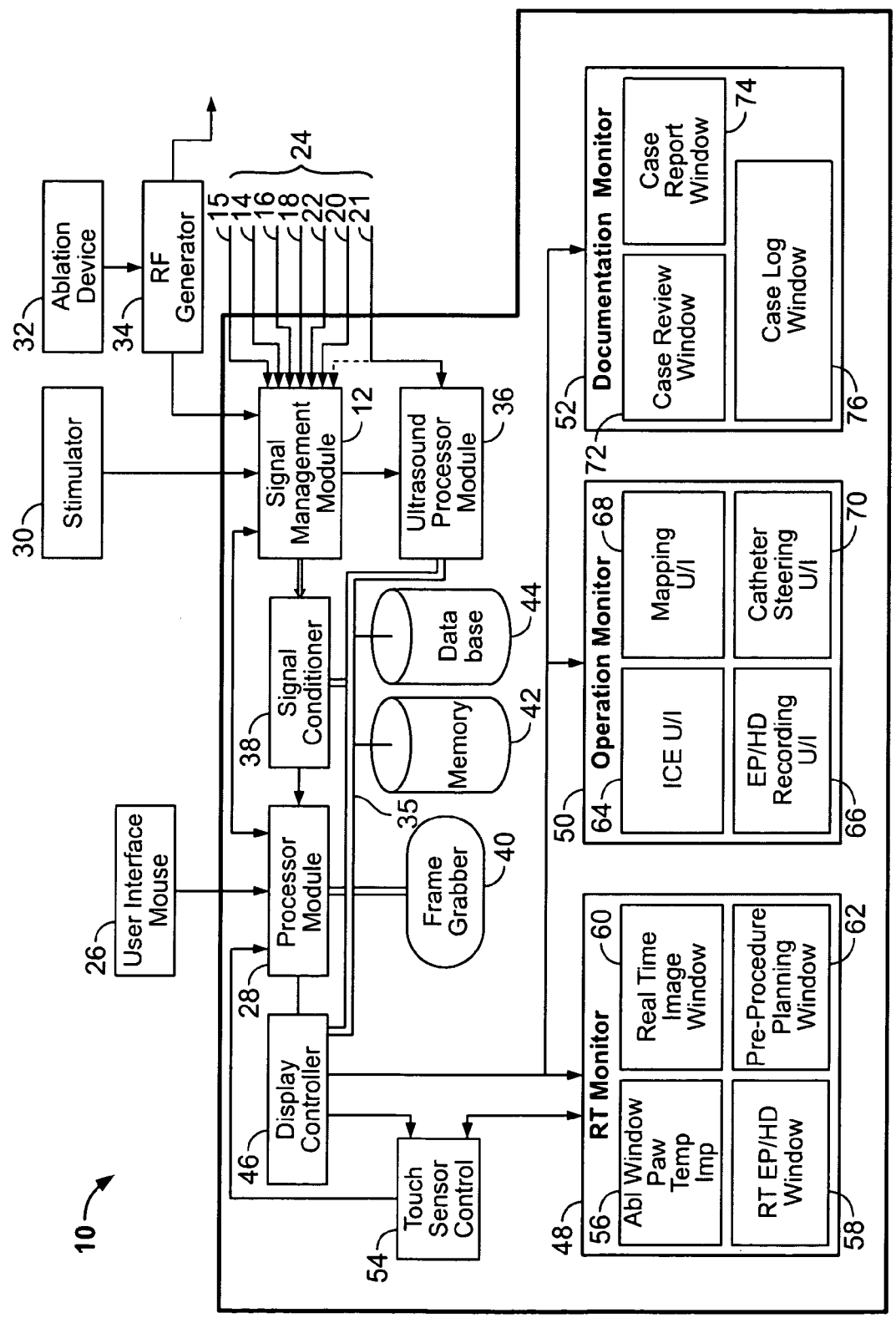
FIG. 1 illustrates a block diagram of a physiology workstation formed in accordance with an embodiment of the present invention.
Figure 2:
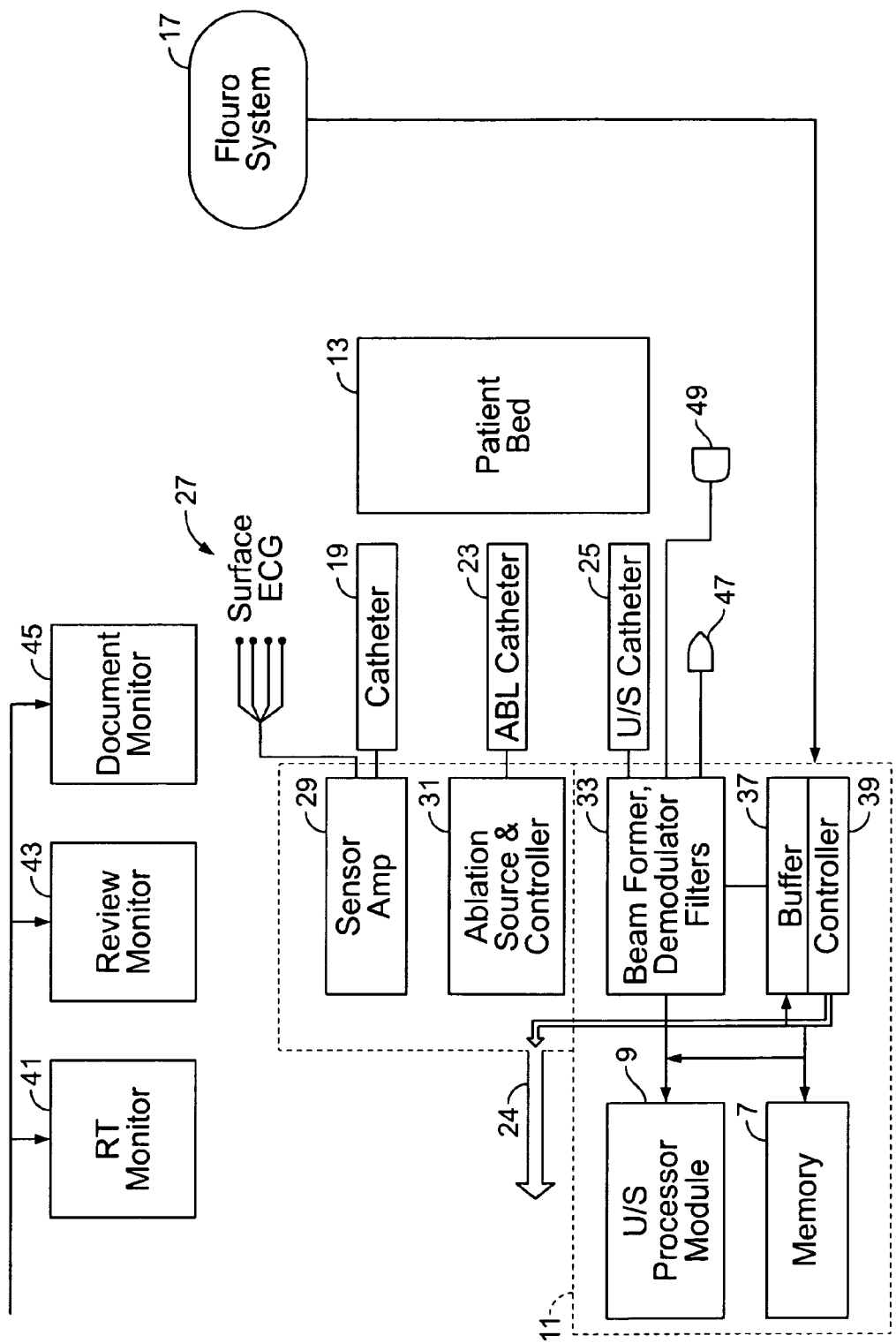
FIG. 2 illustrates a block diagram of ablation and imaging equipment in accordance with an embodiment of the present invention.

FIG. 1 illustrates a physiology workstation 10 formed in accordance with an embodiment of the present invention. The workstation 10 is located in a control room or procedural room and is utilized in connection with HD, EP and ablation procedures, among other things. FIG. 2 illustrates a procedure room which may be separate and discrete from the control room (when used) and from a remote monitoring room within the facility (e.g. a hospital, clinic and the like). The workstation 10 is operated by an operator, while the patient and procedure team are located in the procedure room. The workstation 10 integrates, among other things, real-time information, real-time intracardiac echography, fluoroscopic images, mapping data and pre-surgery planning CT & MR images. The workstation 10 offers integrated monitoring, control and review of HD, EP, patient, and mapping information as well as stored and real-time diagnostic images, ECG signals and IC signals.

As shown in FIG. 2, the procedure room includes an ultrasound system 11, a fluoroscopy system 17 and a patient bed 13 to hold the patient while an HD, EP or ablation procedure is carried out. The fluoroscopy system 17 is provided proximate patient bed 13 to obtain fluoroscopic images of the region of interest while the doctor is conducting a procedure. It is also possible to use a magnetic system to guide catheters, such as by using a magnetic system provided by Stereotaxis, Inc., St. Louis, Mo. A stimulator would be present in an EP configuration. Catheters 19 (EP or HD), an ablation catheter 23 and ultrasound catheter 25 are provided to be inserted or otherwise utilized throughout the procedure. EP catheter 19 performs sensing and stimulating functions. The ablation catheter 23 may represent an RF ablation catheter, a laser ablation catheter or a cryogenic ablation catheter. The ultrasound catheter 25 is configured to obtain ultrasound images of the region of interest, as well as images that indicate directly the position and placement of catheters and the ablation catheter relative to the region of interest or to elucidate anatomy and/or perform measurements such as atrial or ventricular dimension, blood flow through a valve or to obtain other various dimensions and measurements. Surface ECG leads 27 are provided and attached to the patient to obtain surface ECG information. The surface ECG leads 27 and the catheters 19 are joined to a sensor amplifier 29 which amplifies signals sensed by the surface ECG leads 27 and EP catheters 19 prior to transmitting the sensed signals over a communications interface 24. When stimulus pulses are to be delivered to the patient, the stimulus signals are passed either around or through the sensor amplifier 29 to the corresponding catheters 19. An ablation source and controller 31 controls operation of the ablation catheter 23 and provides ablation-related data over the communications interface 24 to the workstation 10 (FIG. 1).

The beamformer 33 is responsible for transmit and receive beam forming operations. The link between the beamformer 33 and ultrasound catheter 25 may comprise individual channels associated with each transducer element within the transducer head of the ultrasound catheter 25. The beamformer 33 controls the phase and amplitude of each transmit signal delivered over the link to induce a transmit or firing operation by the ultrasound catheter 25. Reflected echoes are received at the ultrasound catheter 25 and delivered to the beamformer 33 as analog signals representative of the detected echo information at each individual transducer element. By way of example, the signals transmitted may represent low level analog RF signals transmitted to, or received from, the transducer elements of the ultrasound catheter 25. Optionally, the beamformer 33 may also control transmission and reception in connection with non-catheter type U/S probes, such as a transesophageal probe 47, a surface cardiac probe 49, an intravenous, intraarterial probes and the like.

The beamformer 33 includes a demodulator and filters to demodulate and filter the received analog RF signals and produce therefrom digital base-band I and Q data pairs formed from acquired data samples. The I, Q data pairs are derived from the reflected ultrasound signals from respective focal zones of the transmitted beams. The I and Q data pairs are filtered (e.g. such as in FIR filters that are programmed with filter co-effecients to pass a band of frequencies centered at a desired fundamental frequency of the transmit wave form or at harmonic or sub-harmonic frequencies of the transmit signal's fundamental frequency). The I, Q data pairs corresponds to each data samples within the region of interest. The beamformer 33 may pass the I, Q data pairs to a FIFO buffer 37 which then passes the I, Q data pairs over the communications interface 24 under the control of the controller 39. Alternatively, the beamformer 33 may directly stream the I, Q data pairs over the communications interface 24 as generated without buffering. Optionally, the beamformer 33 may store the I, Q data pairs in memory 7 in the ultrasound system 11. an ultrasound processor module 9 may be provided in the ultrasound system 11 to process the I, Q data pairs to form ultrasound images that are passed over communications interface 24 and/or stored in memory 7.

A real-time monitor 41, a review monitor 43 and documentation monitor 45 are located proximately the patient bed 13 for viewing by the procedure team and physician during the procedure monitors 41, 43 and 45 and are remotely controlled to present the same information as presented on the real-time monitor 48, operation monitor 50 and documentation monitor 52, respectively, located at the workstation 10.

The workstation 10 includes a signal management module 12 which is configured to receive and transmit a variety of signals and data that are conveyed to and from the patient over leads, cables, catheters and the like. Examples of signals that may be received by the signal management module 12 include intercardiac (IC) signals 14 from EP catheters, patient monitoring signals 15 (e.g., from a blood pressure cuff, SPO2 monitor, temperature monitor, CO2 levels and the like), ECG signals 16 from surface ECG leads 27, pressure signals 18 from an open lumen catheter, and intracardiac signals. The signal management module 12 also receives fluoroscopic imaging data 20 from the fluoroscopic system 17, ultrasound imaging data 21 from the beamformer 33, and ablation data 22 (e.g., power, temperature, impedance) from the ablation source and controller 31. The fluoroscopic system 17 is an x-ray apparatus located in the procedure room. The ultrasound data 21 also may be collected at a transesophageal ultrasound probe, an intraoperative ultrasound probe, a transthoracic probe, intravascular probe and/or intracardiac echo probe.

Optionally, the ultrasound system 11 may be operated in an acoustic radiation force imaging (ARFI) mode. ARFI allows examination of the functionality of tissue subsets, such as in the heart, organs, tissue, vasculature and the like. ARFI is a phenomenon associated with the propagation of acoustic waves through a dissipative medium. It is caused by a transfer of momentum from the wave to the medium, arising either from absorption or reflection of the wave. This momentum transfer results in the application of a force in the direction of wave propagation. The magnitude of this force is dependent upon both the tissue properties and the acoustic beam parameters. The duration of the force application is determined by the temporal profile of the acoustic wave. ARFI images the response of tissue to acoustic radiation force for the purpose of characterizing the mechanical properties of the tissue. When the duration of the radiation force is short (less than 1 millisecond), the tissue mechanical impulse response can be observed. ARFI imaging has many potential clinical applications, including: detecting and characterizing a wide variety of soft tissue lesions, and identifying and characterizing atherosclerosis, plaque, and thromboses.

The communications interface 24 extends from the workstation 10 to the various equipment proximate the patient bed. When different rooms are provided the interface 24 extends through the wall or other divider separating the control and procedure rooms, into the procedure room. The communications interface 24 conveys, among other things, IC signals 14, patient monitoring signals 15, surface ECG signals 16, pressure signals 18, fluoroscopic imaging data 20, ultrasound imaging data 21 and ablation data 22. The content and nature of the information conveyed over the communications interface 24 is explained below in more detail. In one embodiment, the communications interface 24 is comprised of physical connections (e.g. analog lines, digital lines, coaxial cables, Ethernet data cables and the like or any combination thereof).

Optionally, the communications interface 24 may include, in whole or in part, a wireless link between the workstation 10 in the control room and one or more of the ultrasound, fluoroscopic, ablation, and EP instruments, devices, apparatus and systems in the procedure room 11. For example, ultrasound data 21 may be communicated wirelessly from a transmitter that is located within the procedure room 11 at the beamformer 33 to a receiver that communicates with the workstation 10 in the control room. The receiver would then convey the imaging data 21 to the signal management module 12.

The signal management module 12 selectively controls access of signals and data onto the communications interface 24. The signal management module 12 may comprise a simple configuration of switches that are manually operated by the user via the user interface 26. Alternatively, switches in the signal management module 12 may be automatically controlled by the processor 28 based upon various criteria including, among other things, the type of procedure currently being conducted. The signal management module 12 may include processing capabilities (e.g. a CPU, DSP and the like) to internally and automatically decide certain switching operations. The signal management module 12 may include memory, such as to temporarily buffer incoming and/or outgoing signals and/or data from/to the communications interface 24. The communications interface 24 conveys analog and digital signals. In the event that the communications interface 24 conveys analog signals, the signal management module 12 may include analog to digital converters to convert the analog signals to digital data and vise versa.

In one embodiment, the beamformer 33 may be located in the procedure room 11 proximate the patient and the ultrasound catheter 25. The beamformer 33 in the procedure room 11 converts the raw echo signals from the individual transducer element channels into I, Q data pairs, each data pair of which represents a data sample. The I, Q data pairs from the beamformer 33 are supplied as the ultrasound data 21 over the communications interface 24 to the workstation 10. The ultrasound data 21 is passed to the ultrasound processor unit 36. In the present example, the U/S processor module 9 is bypassed and not used. The ultrasound data processor module 36 may perform mid-processing operations (e.g., B-mode, Doppler, Strain, ARFI, etc.) upon the ultrasound I, Q data pairs.

In another embodiment, the U/S processor module 9 and the U/S system 11 is used for mid-processing operations and the U/S processing module 36 performs scan conversion operations. In yet another embodiment, the U/S processor modules 9 and 36 at the U/S system 11 and workstation 10, respectively, divide and share the mid-processing operations.

The signal management module 12 may communicate directly with an external stimulator 30. The stimulator 30 may deliver electrical signals (such as for pacing) directly over interface 24, or through the signal management module 12 and the IC leads 14, to one or more catheters 19 positioned within the patient. Examples of stimulators are the Micropace by Micropace Pty Ltd and the Bloom offered by Fisher Imaging.

The workstation 10 is used in an EP study to provide a detailed evaluation of the hearts electrical system. During an EP study, typically 3-5 catheters 19 are used. Each EP catheter 19 includes platinum electrodes spaced near the tip of the catheter, where such electrodes have the ability to record electrical signals from inside the heart as well as deliver stimulus pulses to the heart from different locations, such as to pace the heart. The workstation 10 evaluates normal and abnormal conductions and rhythms. The protocol used during the EP study may vary from site to site or procedure to procedure (e.g. corrected sinus node recovery time, AV Wenckebach and the like).

The stimulator 30 is utilized to induce a pacing train of pulses in order to stabilize a refractory period. The pacing train is considered to have "entrained" the heart once it has captured the heart for a predetermined series of beats. Once the heart is entrained, extra stimuli are added to mimic certain capabilities of the heart. The stimulator 30 may drive ventricular protocols through pacing from a ventricular catheter. One reason for ventricular pacing may be to assess the conduction retrograde through the AV node or bypass tract. When assessing conduction retrograde through the AV node, a VAWBK will also be obtained. Another ventricular protocol is the ventricular effective refractory period (VERPs). The stimulator 30 may also be used to induce arrhythmias. For example, during ventricular protocols, ventricular tachycardia or ventricular fibrillation may be induced as an end point. A patient's level of consciousness is assessed while attempts are made at overdrive pacing (if appropriate). When a patient loses consciousness, an external defibrillation shock is delivered.

The incoming signals from the patient over the communications interface 24 are passed from the signal management module 12 to a signal conditioning circuit 38 which performs various signal processing operations upon the incoming signals. The signal conditioning circuit 38 passes conditioned signals to the processor module 28 and optionally may pass the conditioned signals to a frame grabber 40 or directly to memory 42 or a database 44. The processor module 28 manages overall control and operation of the workstation 10. The processor module 28 receives user inputs through the user interface 26. The processor module 28 stores data, images and other information in the memory 42 and/or in the database 44. The frame grabber 40 also accesses memory 42 and database 44 in order to obtain and store various data, images and the like. While the memory 42 and database 44 are shown as part of the workstation 10, it is understood that one or both of the memory 42 and database 44 may be part of the workstation 10, separate from, but located locally to the workstation 10 (e.g. in the control room) or remote from the workstation 10 and the control room (e.g. in another part of the facility or at an entirely separate geographic location (e.g. a different hospital, university, state, country and the like)).

The memory 42 and database 44 may store diagnostic images, such as CT and MR images acquired prior to the procedure, and ultrasound images acquired prior to, during, or after the procedure. The stored images facilitate pre- and post-procedure analysis for image optimization, manipulation and analysis. The ultrasound images may represent intracardiac ultrasound images obtained from the ultrasound catheter 25. Optionally, the ultrasound images may be obtained utilizing a transesophageal probe 47, an interoperative probe, an intravascular catheter, and an external cardiac probe 49.

Some configurations of the present invention are useful in hemodynamic cases. IVUS is used in such cases to assess the tissue type of occlusions of arteries, for example, whether they are calcified or soft tissue. IVUS is also used to obtain a more accurate percentage of luminal narrowing in arterial disease. ICE may be used in a hemodynamic case to measure the flow across an abnormal opening between chambers of the heart such as patent foramen ovale or an intra-ventrical shunt.

In each of the workstation 10 and U/S system 11, the timing information may be derived from the time of day, or from a reference clock. Alternatively, the various processors may have synchronized clocks which result in all the various systems being synchronized to the identical spot in the cardiac cycle. Alternatively, the timing information may be associated with the cardiac cycle of the patient which is determined by the EP or surface cardiac ECG signals.

The processor module 28 communicates uni-directionally or bi-directionally with the display controller 46 which controls monitors 48, 50 and 52. The monitors 48, 50 and 52 may simply present displayed information as explained hereafter. Optionally, the monitors 48, 50 and 52 may include input buttons for operation by the user to directly enter certain commands and instructions at the monitor 48, 50 and 52. Optionally, the monitors 48, 50 and 52 may represent touch sensitive screens that enable the user to enter information directly by touching active areas of a corresponding monitor 48, 50 and 52.

In the example of FIG. 1, a touch sensor control 54 is illustrated that detects touch actions relative to monitor 48. The touch sensor control 54 provides the results of the touch action to the processor 28. The touch action result may simply represent an X,Y coordinate at which a touch event occurred. Alternatively, the touch sensor 54 may first determine the X,Y coordinate of the touch event and subsequently determine the intended action or instruction based upon the display content of monitor 48 under the control of the display controller 46. For example, the touch sensor control may return a "select drop down menu".

In the example of FIG. 1, monitors 48-52 have been assigned different categories of functions (e.g. real-time monitoring, operations monitoring, documentation monitoring and the like). Monitor 48 presents numerous windows, such as ablation window 56, a real-time EP monitoring window 58, a real-time image window 60 and a preprocessing planning window 62.

The monitor 50 displays windows related to operation control, such as an ICE user interface window 64, an EP/HD recording user interface window 66, a mapping user interface window 68 and a catheter steering user interface window 70. The user interface windows 64-70 allow the operator to enter and change parameters, modes, patient information, values and the like in connection with a particular EP or HD study.

The monitor 52 is configured to present windows associated with documentation of a particular patient case. Monitor 52 presents a case review window 72, a case reporting window 74 and a case log window 76. The case-related windows 72-76 allow the user to review patient history information, as well as current patient information associated with the EP or HD study.

The workstation 10 integrates the display of ultrasound images with other EP or HD study information and/or ablation procedure information by utilizing one or more of monitors 48, 50 and 52. For example, real-time image window 60 may present ultrasound images obtained from an ultrasound catheter or probe, while planning window 62 presents previously acquired CT or MR images. Integrating the ultrasound images into the workstation affords, among other things, an improved standard of care, increased user confidence and shorter procedure time.

Optionally, the real-time image window 60 may present ultrasound images as an image loop, in which a sequence of ultrasound frames is acquired and associated with one or more cardiac cycles. The loop of ultrasound images may be repeatedly displayed or frozen. While the real-time image window 60 presents the ultrasound images, the real-time EP/HD window 58 simultaneously displays real-time EP or hemodynamic signals corresponding to the ultrasound image loop. The planning window 62 may present associated mapping data acquired earlier during the EP or HD study.

The signal management module 12 also communicates directly with an ablation control device 32 which is used to control various ablation procedures. The ablation control device 32 may constitute RF catheter ablation, laser catheter ablation, cryogenic ablation and the like. The ablation device 32 is attached to a generator 34 that produces the energy utilized to achieve ablation. For example, in an RF ablation or laser ablation system, the generator 34 represents a RF generator or a laser source. During RF catheter ablation, energy is delivered from a RF generator through an RF catheter having a tip located proximate anatomy that is desired to undergo ablation. Ablation is generally performed in order to locally destroy tissue deemed responsible for inducing an arrhythmia. The RF energy represents a low-voltage high-frequency form of electrical energy that produces small, homogeneous, lesions approximately 5-7 millimeters in diameter and 3-5 millimeters in depth.

The ablation device 32 may be used in a variety of procedures. The most common type of generic supra ventricular tachycardia (SVT) is atrioventricular nodule reentrant tachycardia (AVNRT). In the most common form AVNRT, the inferior atrianodule input to the atrioventricular (AV) node serves as the anterograde limb (e.g. the slow pathway) of the reentry circuit and the superior antrionodule input serves as the retrograde limb (e.g. the fast pathway). Typically, AVNRT is treated by targeting the slow pathway through ablation near the inferior tricuspid valve annulus at the level of the coronary sinus OS or somewhat higher. Another common type of SVT is orthodramic reciprocating tachycardia (ORT), a reentrant rhythm using the AV node as the anterograde limb and accessory AV connection (e.g. the accessory pathway) as the retrograde limb. The SVT rhythm disturbance can be cured by targeting the accessory pathway as it crosses the mitral or tricuspid valve annulus. Another type of SVT is unifocal atrial tachycardia which may arise in either atrium. The unifocal atrial tachycardia originating in the left atrium is treated through a transsceptal catherization through a foramen ovale or transceptal puncture.

Atrial flutter, another arrhythmia, is most commonly due to a large reentrant circuit in the right atrium, whereby entry proceeds counter clockwise up the atrial septum and down the lateral wall of the right atrium, inscribing inverted flutter waves in the inferior leads. The reentrant circuits associated with atrial flutter used an isthmus of tissue between the tricuspid valve annulus and the inferior vena cava. Linear ablation of the isthmus cures these common forms of atrial flutter. Atrial fibrillation is more commonly treated by crossing the intraarterial septum with a catheter and creating ablation lines in the left atrium which electrically isolates the pulmonary veins. The atrial fibrillation is generally curable and the patient does not require a pacemaker. Ablation may also be performed in connection with ventricular tachycardia.

RF catheter ablation is performed utilizing a sinusoidal high frequency (e.g. 500 kHz) form of electrical current that causes small lesions within the heart. Tissue destruction is primarily caused by thermal injury, such as desiccation necrosis. The RF energy causes resistive heating of a rim of tissue in direct contact with the electrode at the tip of the catheter. Tissue below the surface is heated by conduction of the heat from the para-electrode region. The lesion size is determined by the conduction of the heat through the tissue and by convective heat loss due to the blood pool. In general, the temperature at the interface between the electrode tip and the endocardial tissue should be approximately 50° Celsius or higher in a non-irrigated catheter to cause tissue necrosis. Optionally, the tissue may be heated to higher temperatures. The size and depth of the lesion is controlled by the amount of energy delivered to the tissue. An acute lesion includes a central zone of coagulation necrosis surrounded by a border of hemorrhage and inflammation.

Figure 3:
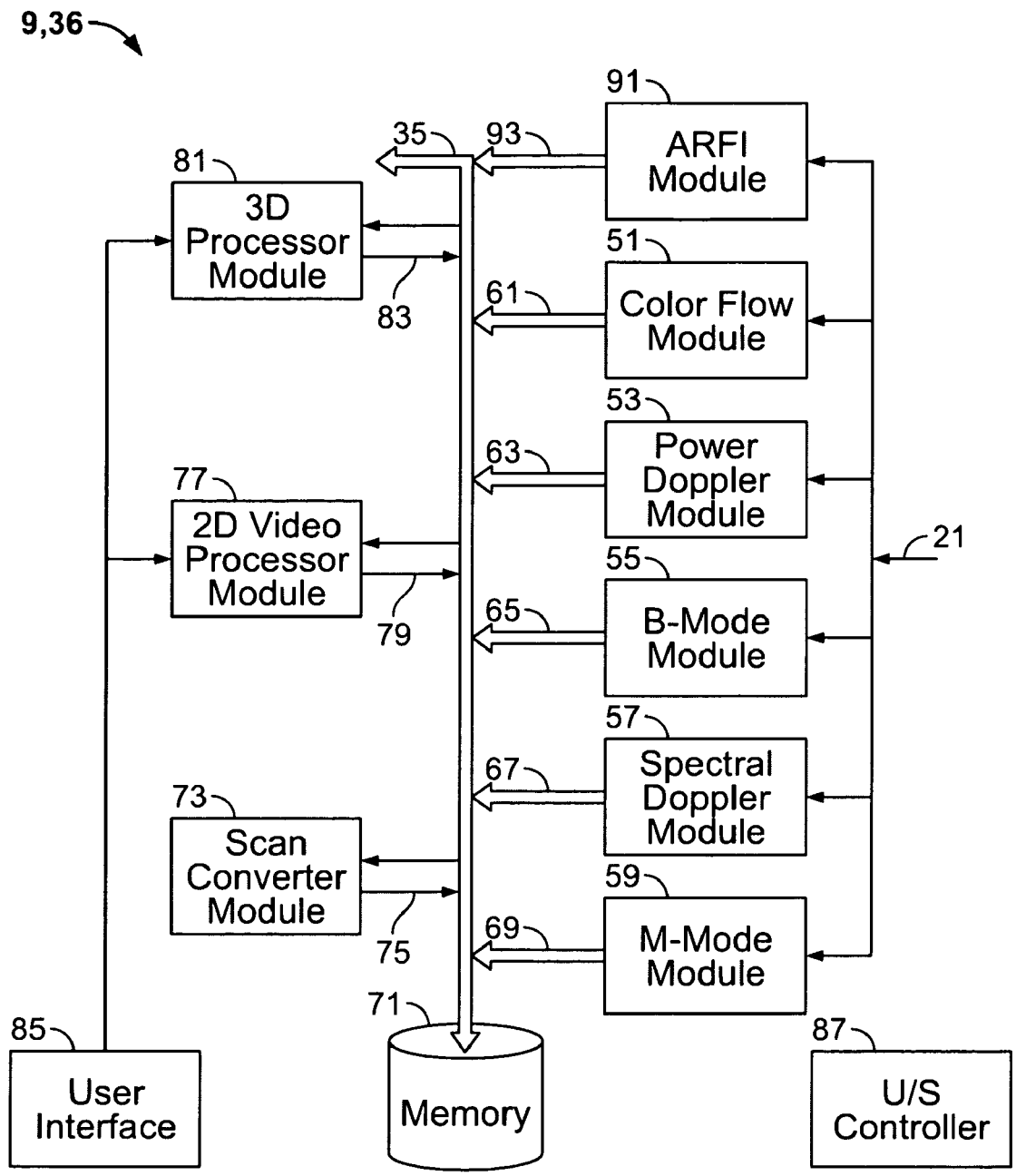
FIG. 3 illustrates a block diagram of the ultrasound processor unit of the workstation of FIG. 1 formed in accordance with an embodiment of the present invention.

FIG. 3 illustrates an exemplary block diagram of the ultrasound processor module 36 of FIG. 1 or the U/S processor module 9 of FIG. 2 formed in accordance with an embodiment of the present invention. The ultrasound processor module 9, 36 is illustrated conceptually as a collection of modules, but may be implemented utilizing any combination of dedicated hardware boards, DSPs and processors. Alternatively, the modules of FIG. 3 may be implemented utilizing an off-the-shelf PC with a single processor or multiple processors, with the functional operations distributed between the processors. As a further option, the modules of FIG. 3 may be implemented utilizing a hybrid configuration in which certain modular functions are performed utilizing dedicated hardware, while the remaining modular functions are performed utilizing an off-the shelf PC and the like.

The operations of the modules illustrated in FIG. 3 may be controlled by a local ultrasound controller 87 or by the processor module 28. The modules 51-59 perform mid-processor operations.

The ultrasound processor module 36 receives ultrasound data 21 in one of several forms depending upon the distribution of ultrasound operations between the ultrasound system 11 and workstation 10. In the embodiment of FIG. 3, the received ultrasound data 21 constitutes I, Q data pairs representing the real and imaginary components associated with each data sample. The I, Q data pairs are provided to a color-flow module 51, a power Doppler module 53, a B-mode module 55, a spectral Doppler module 57 and M-mode module 59. Optionally, other modules may be included such as a strain module, a strain rate module, 3-D or 4-D reconstruction ARFI module and the like. (As used herein, "4-D reconstruction" refers to real-time reconstruction, i.e., images are displayed and updated rapidly so that the delay is short enough to use the images as feedback to make decisions on a procedure being performed at the moment.) Each of modules 51-59 process the I, Q data pairs in a corresponding manner to generate color-flow data 61, power Doppler data 63, B-mode data 65, spectral Doppler data 67, M-mode data 69, and 3-D or 4-D reconstruction ARFI module 91 all of which may be stored in memory 71 temporarily before subsequent processing and/or stored in memory 42 or database 42. The color-flow, power Doppler, B-mode, spectral Doppler and M-mode data 61-69, and 3-D or 4-D reconstruction ARFI data 93 are stored as sets of vector data values, where each set defines an individual ultrasound image frame. The vector data values are generally organized based on the polar coordinate system.

The scan converter module 73 reads from memory 71 the vector data values associated with an image frame and converts the set of vector data values to Cartesian coordinates to generate an ultrasound image frame 75 formatted for display. The ultrasound image frames 75 generated by scan converter module 73 may be passed back to memory 71 for subsequent processing or may be passed to the database 44 (FIG. 1), memory 42 and/or to the processor 28 or display controller 46.

Once the scan converter module 73 generates the ultrasound image frames 75 associated with B-mode data, color-flow data, power Doppler data and the like, the image frames may be restored in memory 71 or passed over bus 35 to the database 44, memory 42 and/or to the processor 28.

As an example, it may be desired to view a B-mode ultrasound image in real-time on the real-time image window 60 on monitor 48 associated with the ultrasound signals detected by an ultrasound catheter 25 (FIG. 2). To do so, the scan converter obtains B-mode vector data sets for images stored in memory 71. The B-mode vector data is interpolated where necessary and converted into the X,Y format for video display to produce ultrasound image frames. The scan converted ultrasound image frames are passed to the display controller 46 which may include a video processor that maps the video to a grey-scale mapping for video display. The grey-scale map may represent a transfer function of the raw image data to displayed grey levels. Once the video data is mapped to the grey-scale values, the display controller 46 controls the real-time monitor 48 to display the image frame in the real-time image window 60. The B-mode image displayed in the real-time image window 60 is produced from an image frame of data in which each datum indicates the intensity or brightness of a respective pixel in the display. The display image represents the tissue and/or blood flow in a plane through the region of interest being imaged.

The color-flow module 51 may be utilized to provide real-time two-dimensional images of blood velocity in the imaging plane. The frequency of sound waves reflected from the inside of the blood vessels, heart cavities, etc., is shifted in proportion to the velocity of the blood vessels; positively shifted for cells moving toward the transducer and negatively shifted for cells moving away from the transducer. The blood velocity is calculated by measuring the phase shift from firing to firing at a specific range gate. Mean blood velocity from multiple vector positions and multiple range gates along each vector are calculated and a two-dimensional image is made from this information. The color-flow module 51 receives the complex I, Q data pairs from the beamformer 33 (FIG. 2) and processes the I, Q data pairs to calculate the mean blood velocity, variance (representing blood turbulence) and total pre-normalized power for all sample volumes within the operator defined region.

The 2D video processor module 77 combines one or more of the frames generated from the different types of ultrasound information. For example, the 2D video processor modules 77 may combine a B-mode image frame and a color-flow image frame by mapping the B-mode data to a grey map and mapping the color-flow data to a color map for video display. In the final displayed image, the color pixel data is superimposed on the grey scale pixel data to form a single multi-mode image frame 79 that is again re-stored in memory 71 or passed over bus 35. Successive frames of color-flow and/or B-mode images may be stored as an image loop in memory 71, memory 42 or database 44. The image loop represents a first in, first out circular image buffer to capture image data that is displayed in real-time to the user. The user may freeze the image loop by entering a freeze command at the user interface 85. The user interface represents a keyboard and mouse and all other commands associated with ultrasound system user interface.

The spectral Doppler module 57 operates upon the I, Q data pairs by integrating (summing) the data pairs over a specified time interval and then sampling the data pairs. The summing interval and the transmission burst length together define the length of the sample volume which is specified by the user at the user interface 85. The spectral Doppler module 57 may utilize a wall filter to reject any clutter in the signal which may correspond to stationery or very slow moving tissue. The filter output is then fed into a spectrum analyzer, which may implement a Fast Fourier Transform over a moving time window of samples. Each FFT power spectrum is compressed and then output by the spectral Doppler module 57 to memory 71. The 2D video processor module 77 then maps the compressed spectral Doppler data to grey scale values for display on the real-time monitor 48 as a single spectral line at a particular time point in the Doppler velocity (frequency) versus a time spectrogram.

A 3D processor module 81 is also controlled by user interface 85 and accesses memory 71 to obtain spatially consecutive groups of ultrasound image frames and to generate three dimensional image representation thereof, such as through volume rendering or surface rendering algorithms. The three dimensional images may be generated utilizing various imaging techniques, such as ray-casting, maximum intensity pixel projection and the like.

Figure 4:
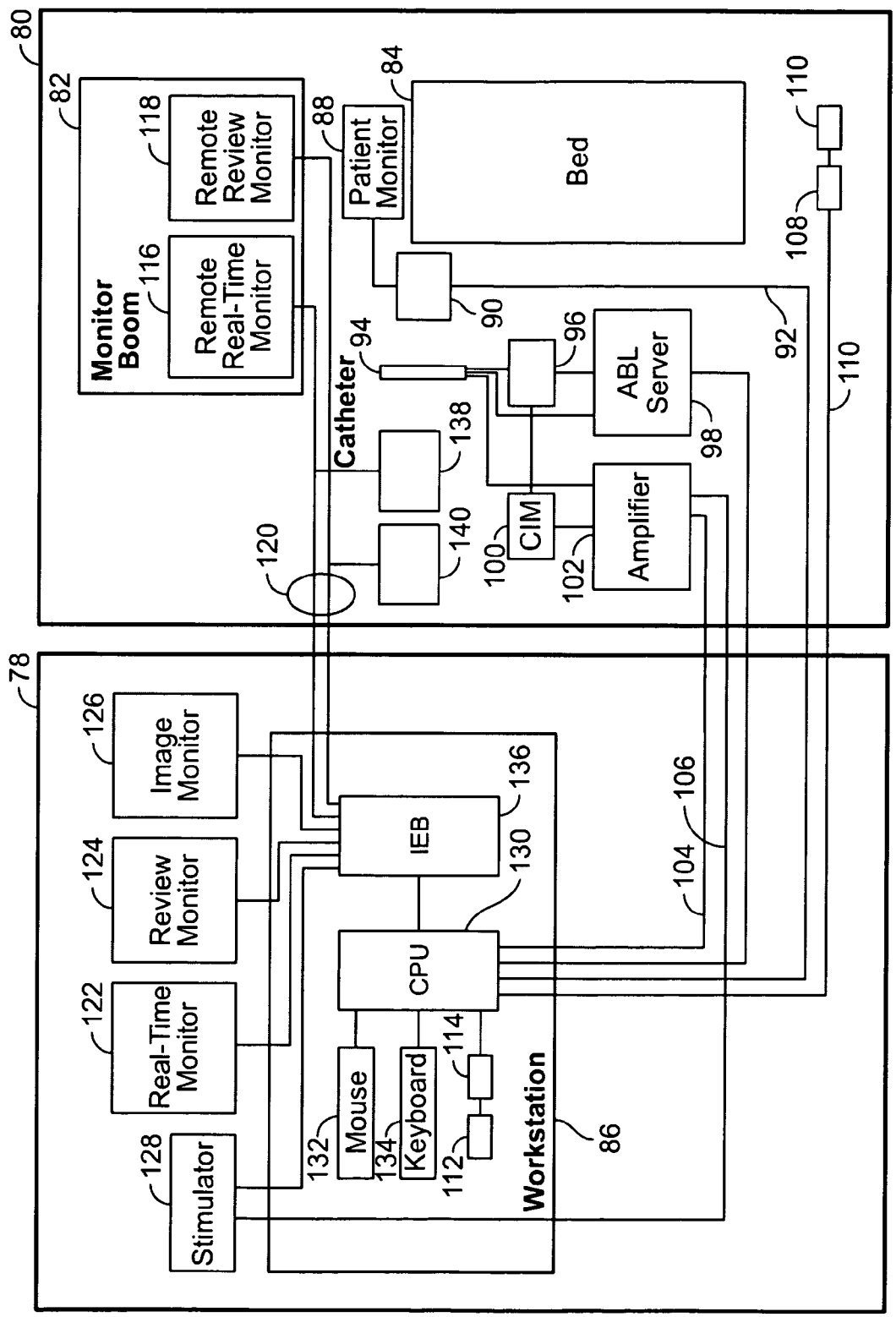
FIG. 4 illustrates a block diagram of an electrophysiology system distributed between multiple rooms within a physiology laboratory in accordance with an embodiment of the present invention.

FIG. 4 illustrates a block diagram of a system configuration for an alternative embodiment distributed between the areas associated with a physiology lab. The lab includes a control area 78 located immediately adjacent a procedure area 80 and a monitoring area 82. The control and procedure areas 78 and 80 may in separate rooms with a window provided between the rooms in order that the operator of a workstation 86 may view of the activities taking place in the procedure room.

The control area 78 includes the workstation 86 that it is joined to a real-time monitor 122, review monitor 124, image monitor 126 and stimulator 128. The workstation 86 includes a CPU 130 that is joined to a mouse 132 and keyboard 134 to facilitate user inputs. A display controller 136 is joined to the CPU 130 control the information and images presented on the monitors 116, 118, 122, 124 and 126. The display controller 136 is also joined directly to the stimulator 128 in order to obtain information associated with stimulus signals.

The procedure area 80 includes a patient bed 84. A patient monitor 88 is located proximate the patient to monitor the patient vital signs. An interface adapter 90 is joined with bedside peripheral devices. The interface adapter 90 enables information from the bedside peripheral devices to be received and processed by the patient monitor 88. The adapter 90 enables the peripheral device information to be displayed, trended and stored at the patient monitor 88. In addition, the interface adapter 90 provides the information, from the peripheral devices, to the workstation 86 over data link 92 which traverses the dividing wall between the procedure area 80 and control area 78. For example, a peripheral device may represent an endtidal $CO_2$ module, that provides information used to guide conscious sedation of the patient.

A catheter 94 is attached to a catheter control module 96, which is joined with an ablation source 98 and a catheter imaging module 100. The catheter imaging module 100 is joined to an amplifier 102. Only one catheter 94 is shown, but multiple catheters 94 or probes may be utilized. The catheters 94 may include one or more EP catheters, ICE catheters, IVUS catheters, ablation catheter, hemodynamic catheters, and the like. The catheters 94 are attached to the catheter control module 96 simultaneously. For example, an EP catheter and an ablation catheter may be joined to the different input ports of the catheter control module 96.

The catheter control module 96 routes signals and data based upon the catheter source. For example, EP signals sensed at the catheter 94 are routed through the amplifier 102 over link 104 to the workstation 86. Stimulus signals from stimulator 128 are delivered, over link 106, through the amplifier 102 or around amplifier 102, to the catheter 94. When catheter 94 represents an ablation catheter, the ablation source 98 delivers the necessary ablation energy (e.g., laser, RF, cryogenic) to the catheter 94. Signals and outputs are read from the ablation source 98 via an output from the ablation catheter designed for this purpose and a serial connection on the ablation device. Optionally, ablation energy may not be routed through the control module 96. When the catheter 94 represents an RF catheter, the ablation source 98 represents an RF signal generator. When the catheter 94 represents a cryogenic ablation catheter, the ablation source 98 supplies a cryogenic medium to the tip of the catheter 94 sufficient to cause tissue necrosis. Optionally, the ablation source 98 may be directly attached to an ablation catheter, thereby circumventing the catheter control module 96.

Speakers 108 and a microphone 110 are provided in the procedure area 80 and joined to the workstation 86 through link 109. The workstation 86 also includes speakers and a microphone 112 and 114 to enable the individuals in the procedure area 80 and in the control area 78 to communicate with one another.

The monitor area 82 includes one or more monitors, such as a real-time monitor 116 and a remote review monitor 118. The real-time and remote review monitors 116 and 118 are joined to the workstation 86 over links 120 present, to the people in the monitor area 82, the same information as illustrated on the real-time monitor 122 and review monitor 124 in the control area 78. An image monitor 126 is also provided in the control area 78, and may similarly be duplicated in the monitor area 82.

Optionally, the procedure area 80 may include one or more slave monitors, such as slave real-time monitor 138 and slave review monitor 140. The slave monitors 138 and 140 enable personnel in the procedure room to easily visualize the real-time IC signals, surface ECG signals, hemodynamic waveforms, ultrasound images and the like.

Figure 5:
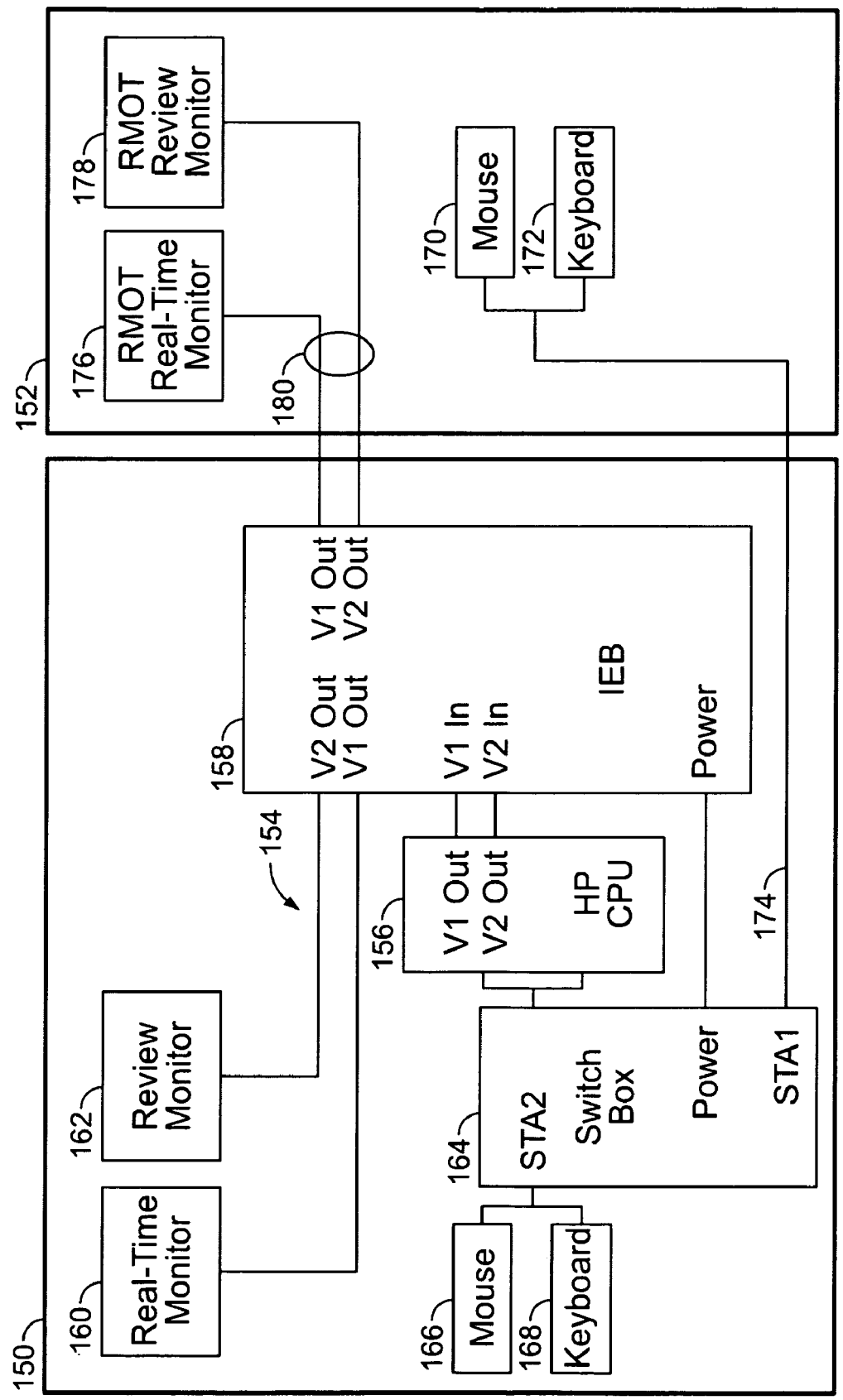
FIG. 5 illustrates a block diagram of an alternative physiology system distributed between multiple rooms within a laboratory in accordance with an embodiment of the present invention.

FIG. 5 illustrates an alternative embodiment configured to provide remote operator control. In FIG. 5, a control room 150 separated from a procedure room 152. The control room 150 includes a workstation 154 having a processor 156 that communicates with a display controller 158 to display information on real-time monitor 160 and review monitor 162. A switch box 164 interconnects a mouse and keyboard 166 and 168 with the CPU 156. The mouse and keyboard 166 and 168 are located at the workstation 154 in the control room 150 to facilitate user inputs and control. The switch box 164 is also joined, over a remote link 174, to a mouse and keyboard 170 and 172 which are provided in the procedure room 152. The mouse and keyboard 170 and 172 are located remote from the workstation 154 and a separate room, namely the procedure room 152. A remote real-time monitor 176 and a remote review monitor 178 are also provided in the procedure room 152 remote from the workstation 154. The remote real-time monitor 176 and review monitor 178 are controlled over remote links 180 by the display controller 158.

The remote mouse and keyboard 170 and 172 and the remote real-time and review monitors 176 and 178 allow a user to enter data or control functions of the ultrasound system directly into the workstation 154 via a specialized mouse or mouse and keyboard combination through switch 164. The switch 164 automatically switches between the local and remote mouse and keyboard 166, 168 and 170, 172 such that only one combination of mouse and keyboard is active at any point in time.

Figure 6:
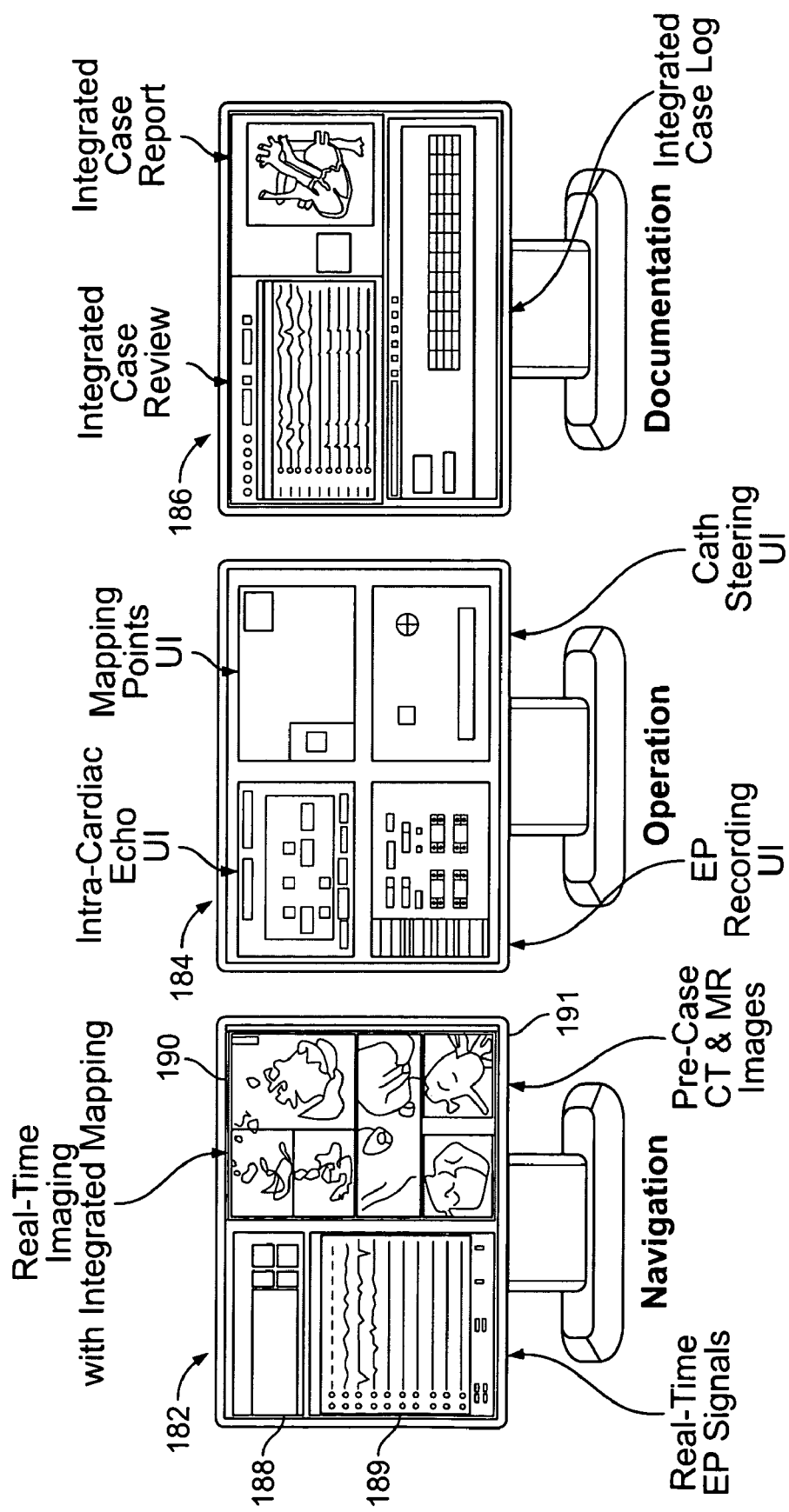
FIG. 6 illustrates exemplary window layout for a configuration of monitors for a physiology workstation formed in accordance with an embodiment of the present invention.

FIG. 6 illustrates more detailed examples of the window content that may be presented in various combinations on the monitors 48-52, 116-118, 122-126, 160-162 and 176-178. The monitors in FIG. 6 represent a navigation monitor 182, an operations monitor 184 and a documentation monitor 186. The navigation monitor includes an ablation window 188, real-time EP signal window 189, real-time imaging window 190 with integrated mapping indicia and pre-case image window 191 (e.g. previously acquired CTR MR images). The operations monitor 184 includes windows associated with intracardiac echography, mapping, catheter steering and EP recording. The documentation monitor 186 includes windows associated with integrated case review, integrated case reports and an integrated case log.

Optionally, the beamformer 33 may be moved from the procedure room 11 and located at the ultrasound processor unit 36. In this embodiment, the ultrasound data 21 would represent raw echo signals conveyed over separate channels from each transducer element of an ultrasound device (e.g. probe or catheter). The raw echo signals from the transducer elements would not undergo beam-forming before arriving at the workstation 10. For example, the ultrasound catheters 19 may include a transducer having 64 elements and thus 64 separate channels may be organized within the ultrasound data 21. The raw echo ultrasound data 21 would then be routed to the ultrasound data unit 36 to perform beamforming processing to generate I, Q data pairs and from that generate ultrasound vector data sets, each set of which corresponds to a 2D image frame. The ultrasound vector data sets may include one or more of B-mode data, color flow data, power Doppler, 3-D or 4-D reconstruction, and the like. The ultrasound vector data sets may be stored directly in the database 44 and/or memory 42. The ultrasound vector data sets may be passed through signal conditioner 38 to processor 28.

Figure 7:
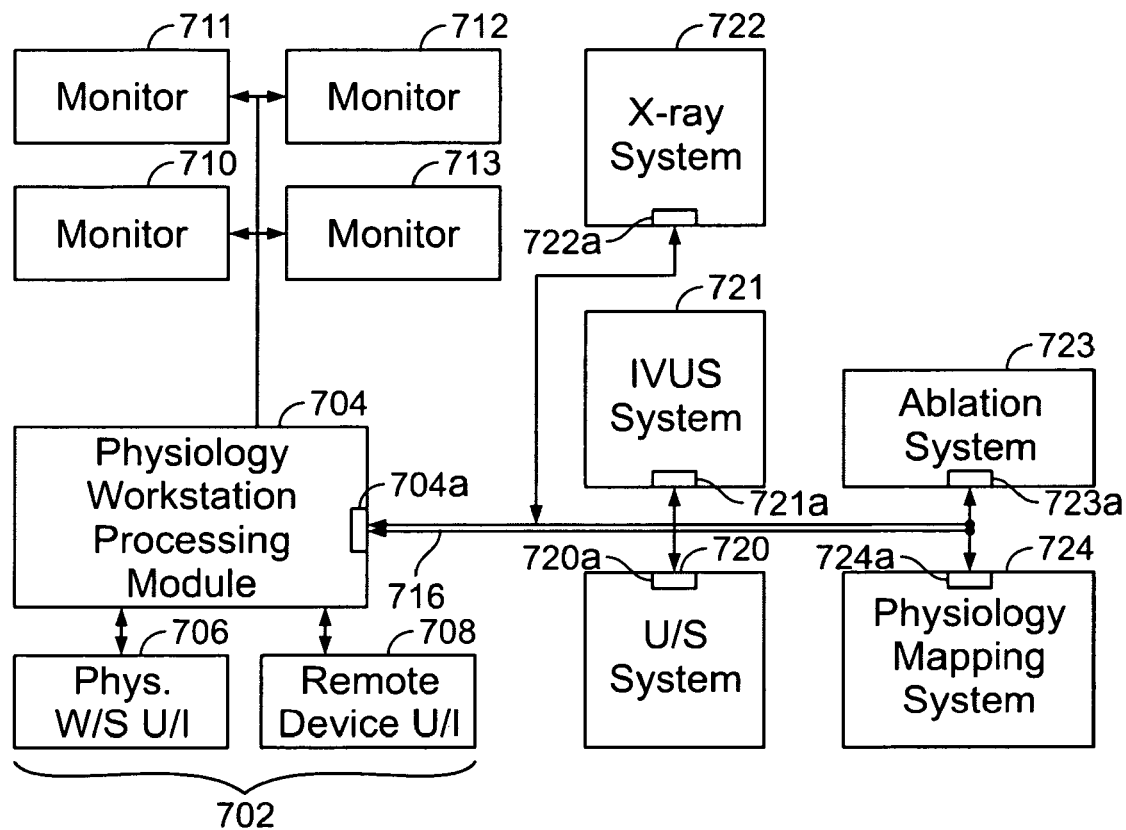
FIG. 7 illustrates a block diagram of an alternative embodiment in which remote control is provided for various systems and devices formed in accordance with an embodiment of the present invention.

FIG. 7 illustrates a block diagram of an alternative embodiment in which remote control is provided for various systems and devices. In FIG. 7, a physiology workstation 702 (e.g. EP or H. D. workstation) and includes a physiology workstation processing module 704 that communicates with, and is controlled by, a physiology workstation user interface 706. The physiology workstation 702 may be located in a new separate room (e.g. a control room) remote from the systems 720-724. Alternatively, the physiology workstation 702 may be located in the same room as the systems 720-724. A remote device user interface 708 also communicates with the physiology workstation processing module 704. The monitors 710-713 are joined to the physiology workstation processing module 704 to illustrate the various information, images, signals, and the like explained above. A link 716 is maintained between the physiology workstation processing module 704 and various remote devices, such ultrasound system 720, IVUS catheter 721, x-ray system 722, ablation system 723 and physiology mapping system 724. The systems 720-724 may each include the associated types of acquisition apparatus (e.g. catheters, probes, C-arm, coils and the like, as well as monitors and user interfaces).

The link 716 may include one or more links connected to each of the systems 720-724. For example, the link 716 may include a single serial or parallel line directly extending from the remote device user interface 70821 of the systems 720-724, and attached thereto, at a user interface input. Alternatively or in addition, link 716 may include a data bus conveying serial or parallel data between the processors within module 704 and one or more of systems 720-724 (e.g. ECG data, EP data, HD data, image frames and the like). The link 716 may also include one or more video cables extending between a video output (e.g. VGA) at one of systems 720-724 and a video input at one or more of monitors 710-713.

Optionally, the link 716 may constitute a network connection, such as supporting an Internet protocol (IP) or the transmission control protocol (TCP), or other protocols. The data may be transmitted over link 716 as raw ultrasound or x-ray data, formatted in the Hypertext markup (HTML) language, and the like. Optionally, the link 716 may be constructed as a local area network configuration, a client/server configuration, an intranet configuration, a file sharing configuration and the like. Communications modules 704a and 720a-724a would be provided at each of the module 704 and systems 720-724 configured in accordance with the appropriate configuration. The communications modules 704a and 720a-724a may represent USB ports, while the link 716 represents a USB cable. Alternatively, the communications modules 704a and 720a-724a may represent serial or parallel connectors, HSSDC connectors, Fiber Channel connectors and the like, while the link 716 represents the corresponding type of communications medium. Alternatively, the link 716 may be wireless (e.g., RF, Bluetooth, etc.).

The remote device user interface 708 may be used to control the operation of one or more of the systems 720-724. For example, the remote device user interface seven OA may be used to enter system parameters, settings, modes, create measurements and the like. The remote device user interface 708 permits the operator of the physiology workstation 702 to remotely control the operation, and remotely adjust the settings, modes and parameters, of one or more of the systems 720-724. The remote device user interface 708 improves workflow within the procedure room, increases productivity of an EP or HD team in the procedure room and end the review room, and decreases the overall procedure duration.

By way of example, when the remote device user interface 708 is used in connection with control of the ultrasound system 720 or IVUS or ICE catheter or probe 721, the remote operator may be afforded the ability to change a modes, adjust the gain of the ultrasound probe or catheter, freeze select images on the monitor at the physiology workstation 702 and the monitor at the ultrasound system 720, and the like. Optionally, the remote device user interface 708 may constitute a dedicated keyboard identical to a keyboard provided with one of systems 720-724. In some configurations of the present invention, the remote device may comprise a specialized mouse and multifunction keys combined with soft key functions on the remote device. As used herein, the term "soft keys" refers to icons on a computer screen that emulate buttons on the remote device and which may be activated by the mouse and/or one or a combination of keyboard keys.

Figure 8:
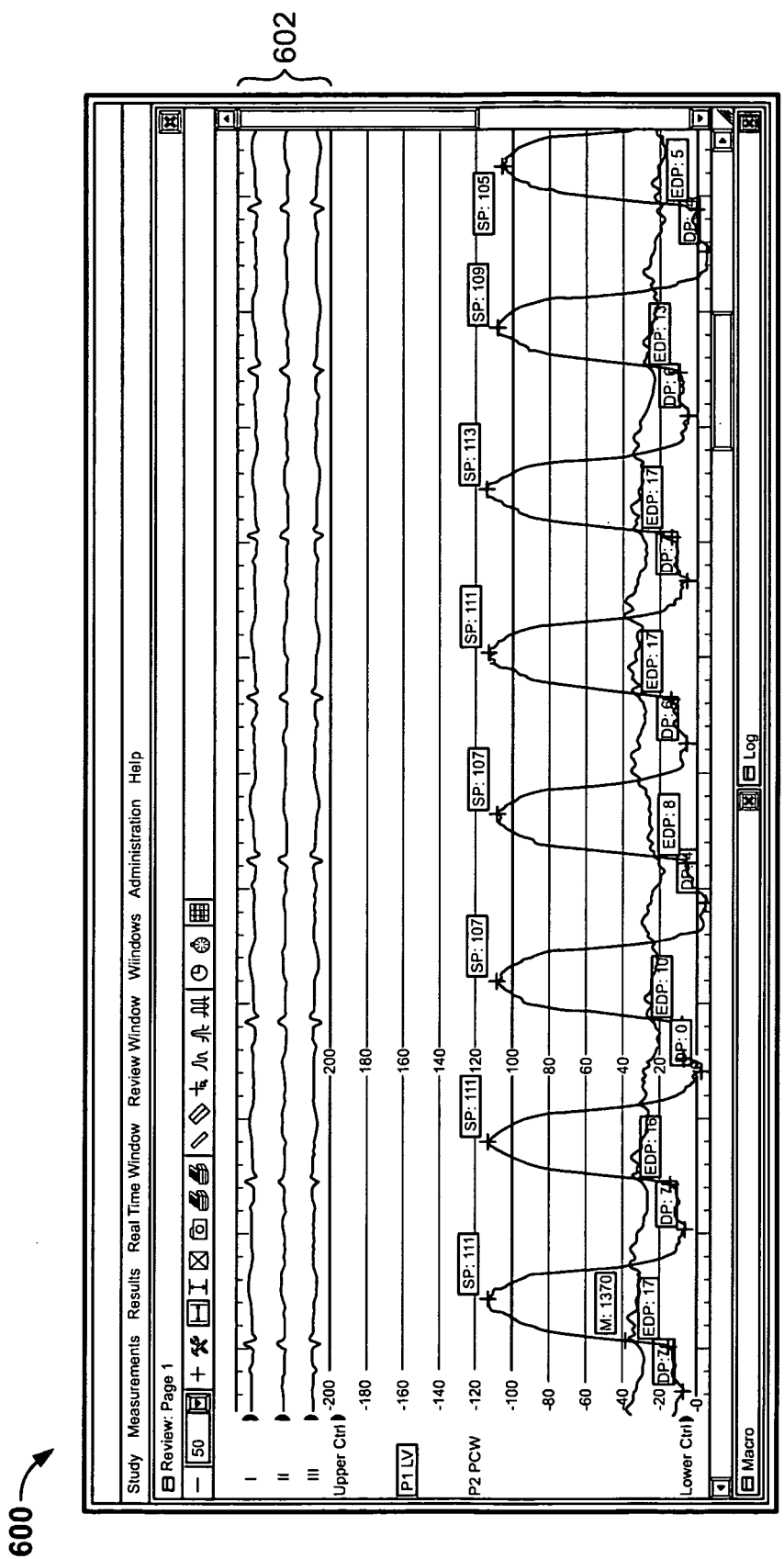
FIG. 8 illustrates a screenshot of an exemplary window presented on one of the monitors of the physiology workstation formed in accordance with an embodiment of the present invention.

FIG. 8 illustrates a screenshot of an exemplary window presented on one of the monitors of the physiology workstation. The screenshot of FIG. 8 represents a hemodynamic window 600, including three ECG traces, above a graph plotting the pressure at a particular point within the heart. In the example of FIG. 8, the pressure information is being obtained from an open lumen catheter having an outer end located proximate the mitral valve. The peaks and valleys within the graph represent the diastolic points (DP) and systolic points (SP) in the cardiac cycle. The pressure at each DP and SP is indicated as well. The EDP represents the end diastolic pressure. Along the bottom of the graph are a series of time stamps identifying the time (relative to the system clock) at which each pressure point was measured. The upper and lower controls (UpperCtrl and LowerCtrl) may be adjusted by the operator to adjust the dynamic range over which the pressure is measured.

In some embodiments the physiology workstation is connected either via direct connection to an ultrasound system utilizing fiber optic or standard networking cabling allowing bi-directional communication between the two systems using standard protocols. This connection allows remote control of the ultrasound system via the user interface of the physiology workstation. Ultrasound functions such as changing modes, changing gain, measurements, storing of images, etc can be controlled via the physiology workstation. In addition the clocks of the two systems are synchronized allowing the user to know that data points that occur at discreet points in time represent data collected simultaneously. Images and measurements may be stored to the physiology workstation and displayed to the user concomitant with other data obtained by the physiology workstation.

Also, in some configurations, a physiology workstation is provided that comprises a communications interface conveying physiology signals derived from a subject and ultrasound data representative of a region of interest of the subject. The ultrasound data is obtained by an ultrasound device in real-time during a procedure carried out on the subject. A processing unit receives and processes the physiology signals. An ultrasound processing unit receives and processes the ultrasound data to generate ultrasound images. The processing unit combines the physiology signals with the ultrasound images from the ultrasound processing unit. A display unit displaying the physiology signals and the ultrasound images. The physiology signals and ultrasound signals are presented jointly to a user in real-time during the procedure being carried out on the subject. The ultrasound system is controlled via hardware and software keys on the EP or HD system. The EP or HD system is configured to pass commands to the ultrasound system, which displays the results of those commands on both the ultrasound and EP or HD system. The ultrasound system is configured to be controlled either via the EP or HD system or from controls directly on the ultrasound system.

Figure 9:
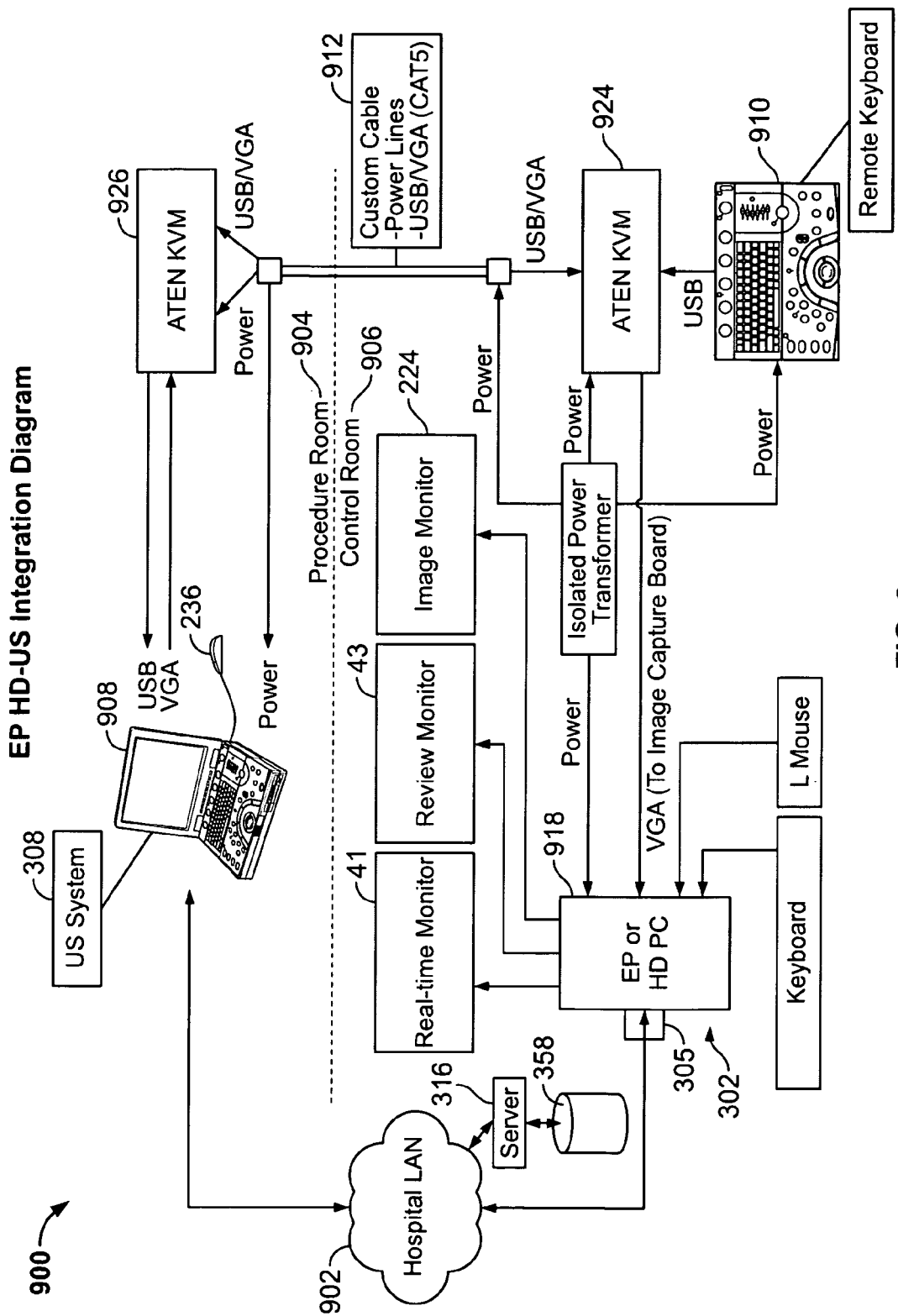
FIG. 9 illustrates a block diagram of a physiology network having a remote physical keyboard and formed in accordance with an embodiment of the present invention, wherein the remote physical keyboard provides keys corresponding to all or nearly all the functionality of an associated ultrasound system.

More particularly, and referring to FIG. 9, in some configurations of the present invention, a physiological network 900 is provided that is configured to operate with a medical network 902. An ultrasound system 308 is located in a procedure room 904. Ultrasound system 308 includes an ultrasound probe 236. A physiological workstation 302 (also referred to herein as a "local workstation") is configured to operate in a procedure room 906 and is operatively coupled via medical network 902 to display ultrasound signals obtained from a subject during an ultrasound procedure carried out on the subject. Local workstation 302 has a network interface 305 configured to communicatively couple to medical network 902. A database 358 storing patient records associated with the subject undergoing the physiological procedure is also provided. A server 316 is operatively coupled to medical network 902 and database 358. Server 316 is configured to provide, to a local workstation 309 (which can be a display on ultrasound system 308) and remote workstation 302, a patient record associated with the subject. Local workstation 309 co-displays the ultrasound signals and information from the patient record to an operator of local workstation 309. A remote workstation 302 is configured to operate in a control room 906 different from procedure room 904, so that a person in the control room can control ultrasound system 308 while receiving, processing, and displaying the ultrasound signals obtained from the subject in real-time 41, while an ultrasound procedure is being performed on the subject. Remote workstation 302 can comprise an EP workstation, an HD workstation, or a combination EP/HD workstation. Ultrasound probe 236 can be, for example, an intravascular ultrasound probe, and ultrasound system 308 can be, for example, a 2-D ultrasound system or a 3-D ultrasound system. In some configurations, remote workstation 302 and either or both local workstation 908 or ultrasound system 308 have synchronized clocks. These clocks (which may comprise embedded software or firmware modules) can be synchronized, for example, to the time on server 316.

Figure 10:
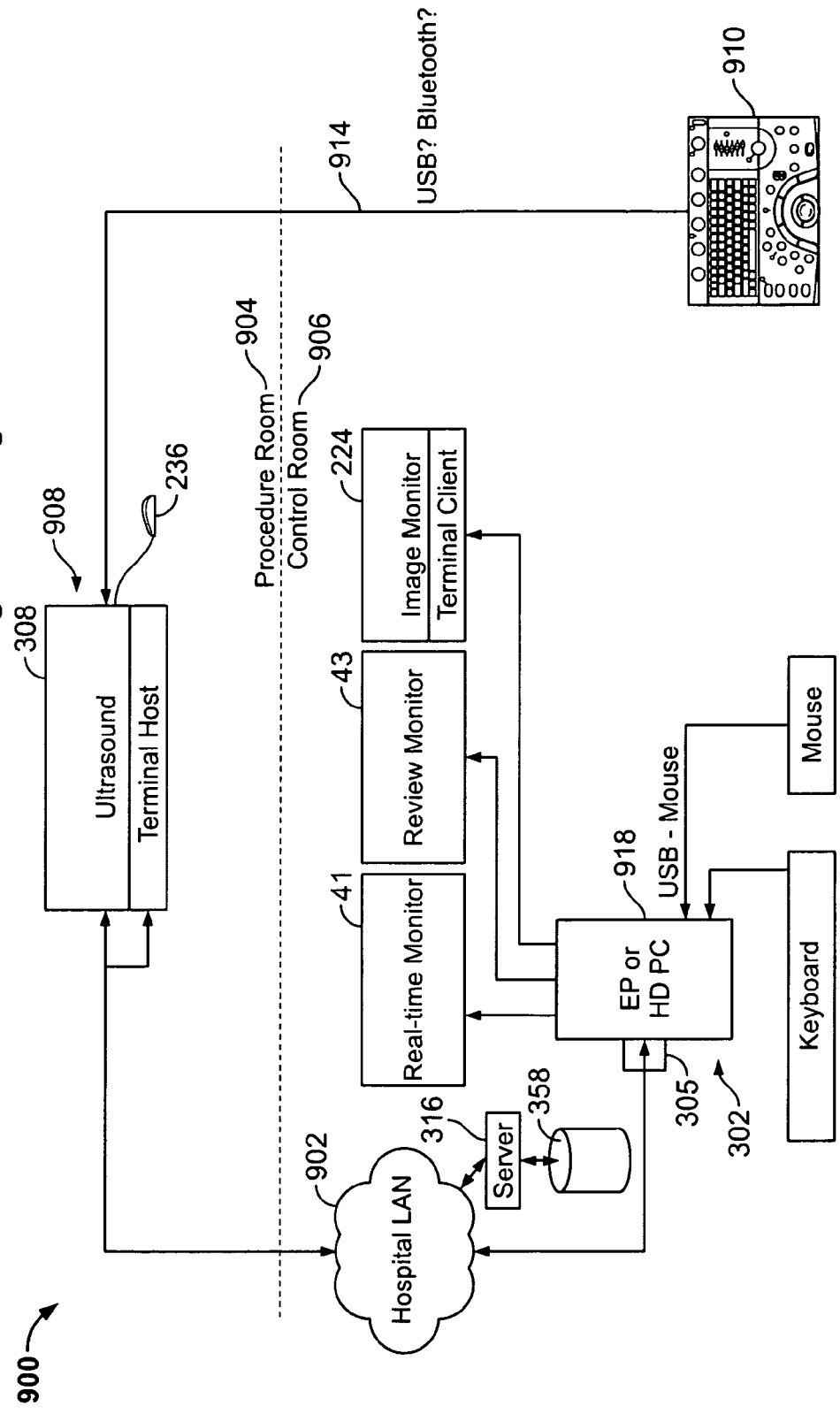
FIG. 10 illustrates a block diagram of a physiology network having a remote keyboard configured to communicate with the ultrasound system via a wired or wireless connection separate from a medical network.

In some configurations of the present invention, a keyboard 910 is provided in control room 906. Keyboard 910 is configured to communicate with ultrasound system 308 via either a wired connection 912 separate from medical network 902 or a wireless connection 914 (see FIG. 10) separate from medical network 902. Wired connection 912 can be, for example, a custom cable or a USB connection. Wireless connection 914 can be, for example, any of the 802.11 wireless protocol connections or a bluetooth connection.

Figure 11:
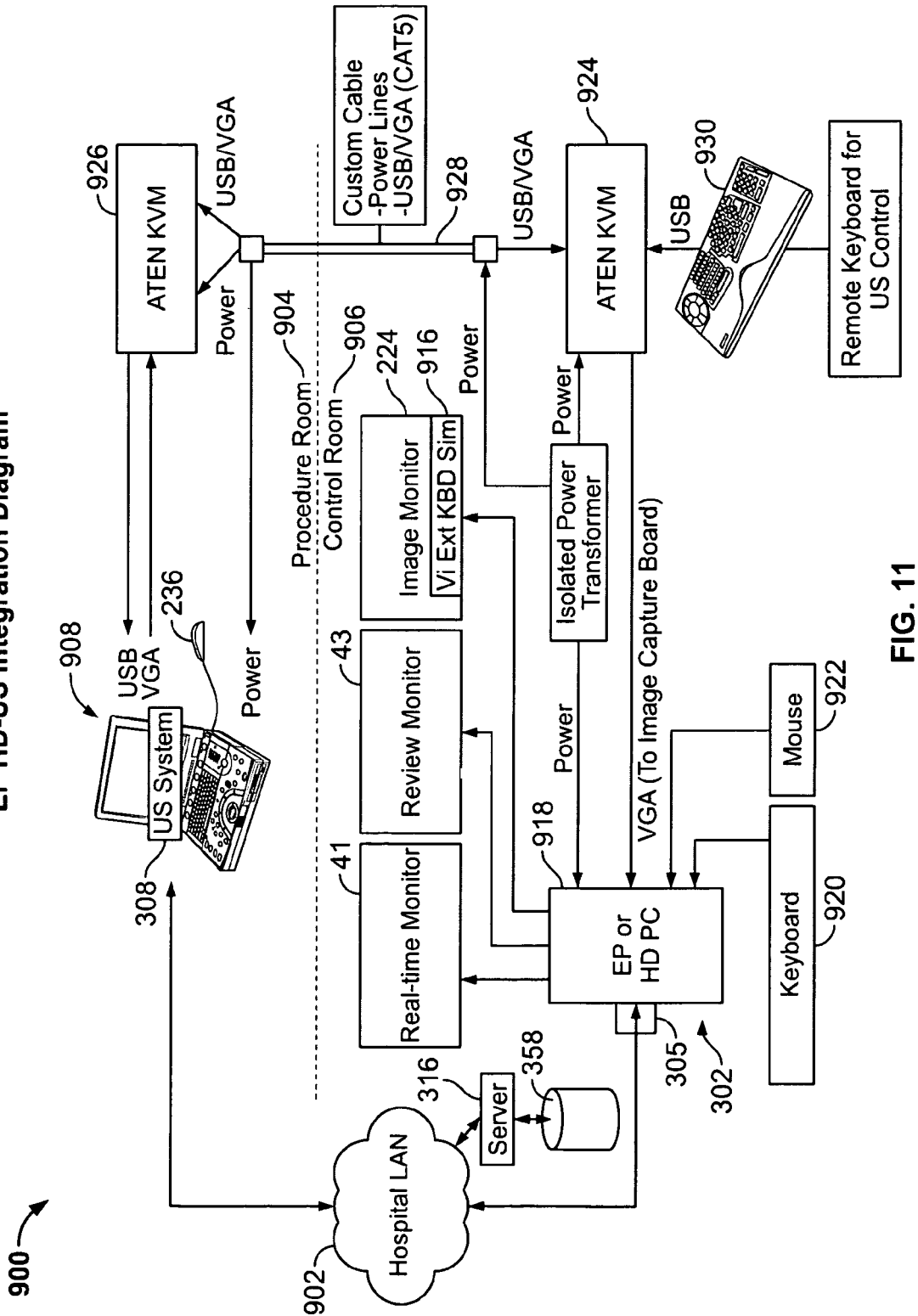
FIG. 11 illustrates a block diagram of a physiology network having a visual keyboard simulator software module configured to run, at least in part, on the remote (physiological) workstation, to display a simulated keyboard on an image monitor, and to communicate with the local (ultrasound) workstation to thereby control the ultrasound system. Also, the remote physical keyboard is a standard PC-style keyboard having either fewer or different keys than the remote physical keyboard shown in FIG. 10.

Also, in some configurations of the present invention and referring to FIG. 11, remote workstation 302 includes an image monitor 224 and a visual keyboard simulator software module configured to run, at least in part, on remote workstation 302. (To receive simulated keypresses, a portion of the keyboard simulator software module may be configured to run on local workstation 908 in some configurations.) An image 916 of a keyboard is displayed on image monitor 224.

Image monitor 224 may include a touchscreen for operating the keyboard simulator from image 916, or EP or HD PC 918 may be configured to activate simulated keypresses on image 916 using a separate physical keyboard 920 or mouse 922. Virtual keypresses from keyboard 916 are transferred through medical network 902. In some configurations, a pair of keyboard/video/mouse (KVM) switches 924, 926 and a custom cable 928 are provided to communicate between a remote keyboard 930 and ultrasound system 308. However, because some KVM switches 924, 926 are unable to effectively communicate signals that control ultrasound system 308. Therefore, signals that control ultrasound system 308 are generated by the visual keyboard simulator software module in response to simulated keypresses and transmitted via LAN 902 to ultrasound system 308.

Figure 12:
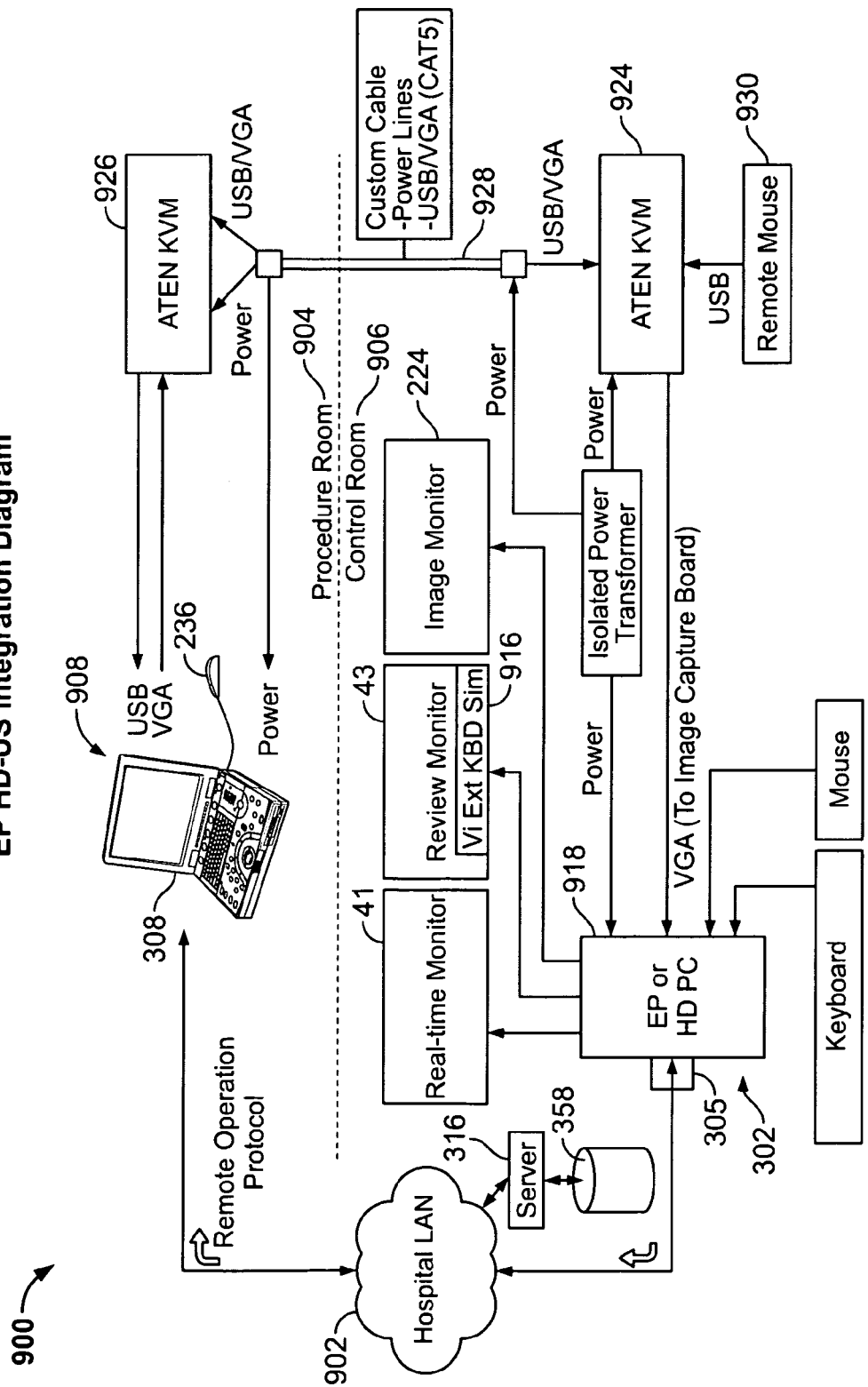
FIG. 12 illustrates a block diagram of a physiology network having a visual keyboard simulator software module configured to run, at least in part, on the remote (physiological) workstation, to display a simulated keyboard on a review monitor, and to communicate with the local (ultrasound) workstation to thereby control the ultrasound system.

In some configurations and referring to FIG. 12, the keyboard simulator software module is configured to display keyboard image 916 on review monitor 43 instead of, or in addition to, image monitor 224. Review monitor 43 may comprise a touchscreen.

Figure 13:
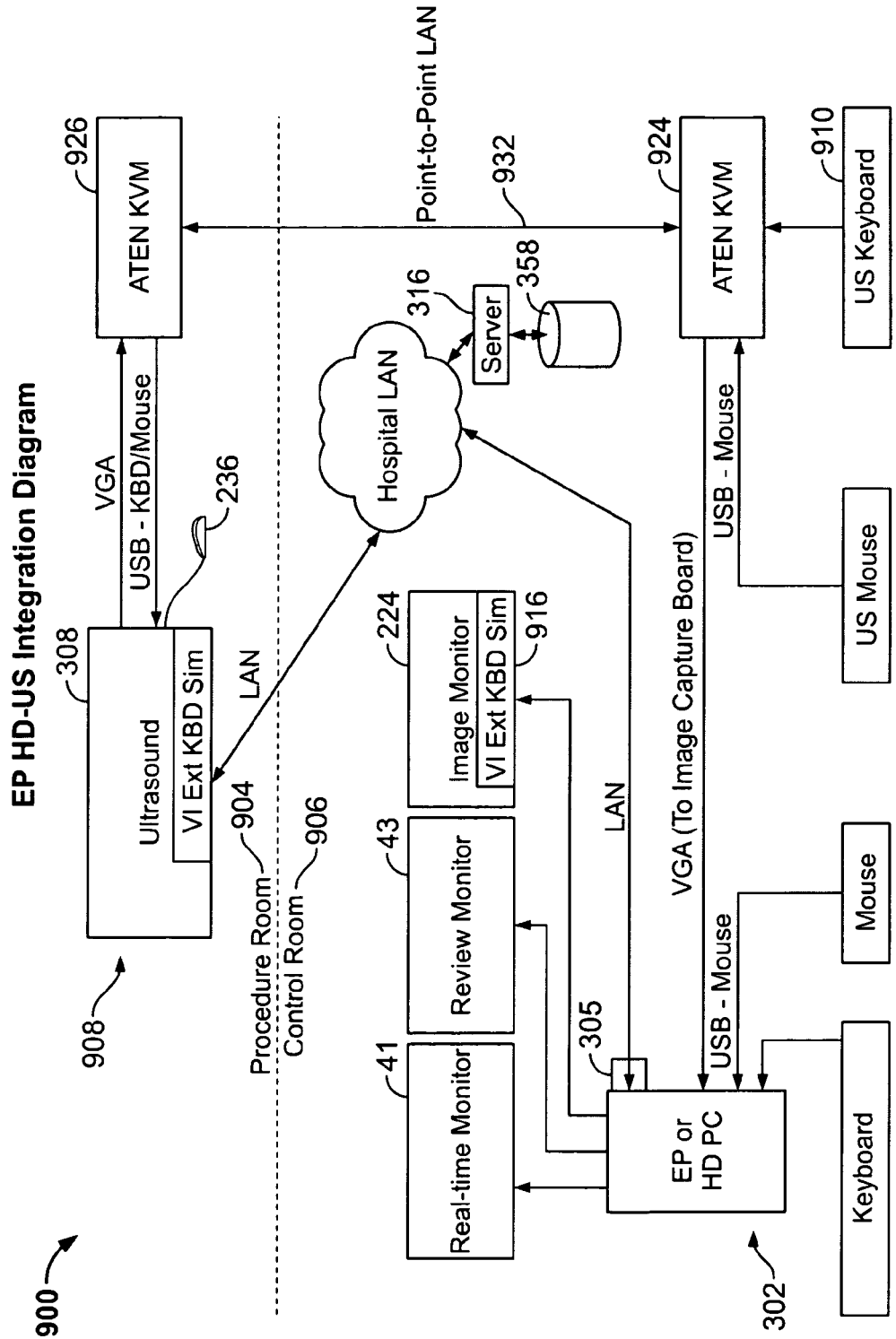
FIG. 13 illustrates a block diagram of a physiology network having a visual keyboard simulator software module configured to run, at least in part, on the remote (physiological) workstation, to display a simulated keyboard on an image monitor, and to communicate with the local (ultrasound) workstation to thereby control the ultrasound system. A remote keyboard that is configured to communicate signals other than control signals to the ultrasound system via a wired or wireless connection separate from a medical network is also provided.

In yet another configuration or configurations and referring to FIG. 13, a pair of KVM switches 924, 926 is provided and a point-to-point wired or wireless local area network (LAN) 932 configured to communicatively couple local workstation 908 to remote workstation 302 is also provided. Data communicated via KVM switches 924, 926 and LAN 932 exclude control signals resulting from use of the visual keyboard simulator software module for controlling ultrasound system 308. Such control signals are instead communicated, for example, via medical network 902.

Figure 14:
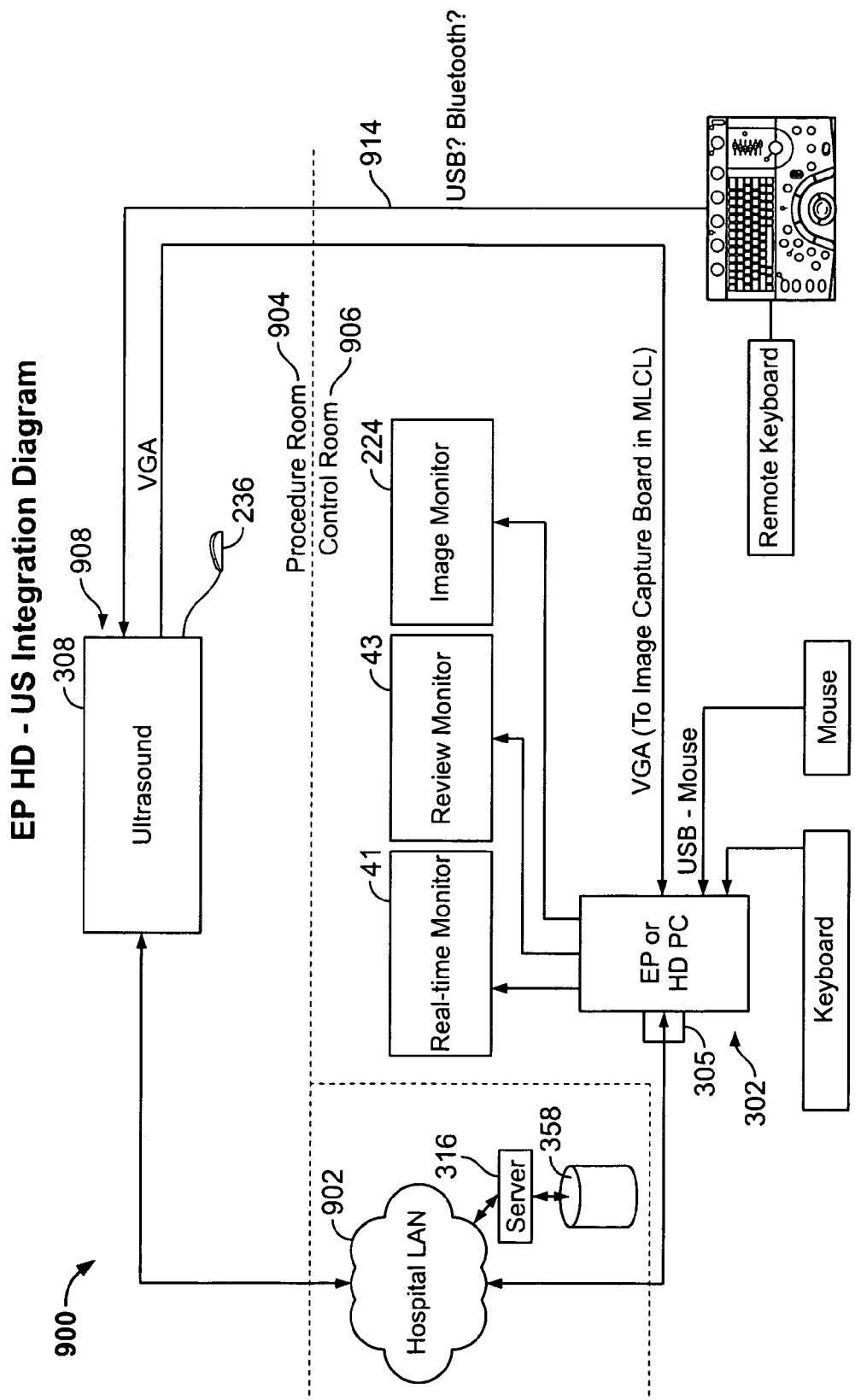
FIG. 14 illustrates a block diagram of a physiology network wherein the remote keyboard is directly connected to the ultrasound system via a wired or wireless connection other than the medical network.

In some configurations and referring to FIG. 14, a keyboard 910 in control room 906 is configured to communicate with ultrasound system 308 via a connection 914 separate from medical network 902. Connection 914 is either (or both) a wired connection (such as a USB connection) separate from medical network 902 or a wireless connection (e.g., bluetooth, 802.11 wireless) separate from the medical network 902.

Figure 15:
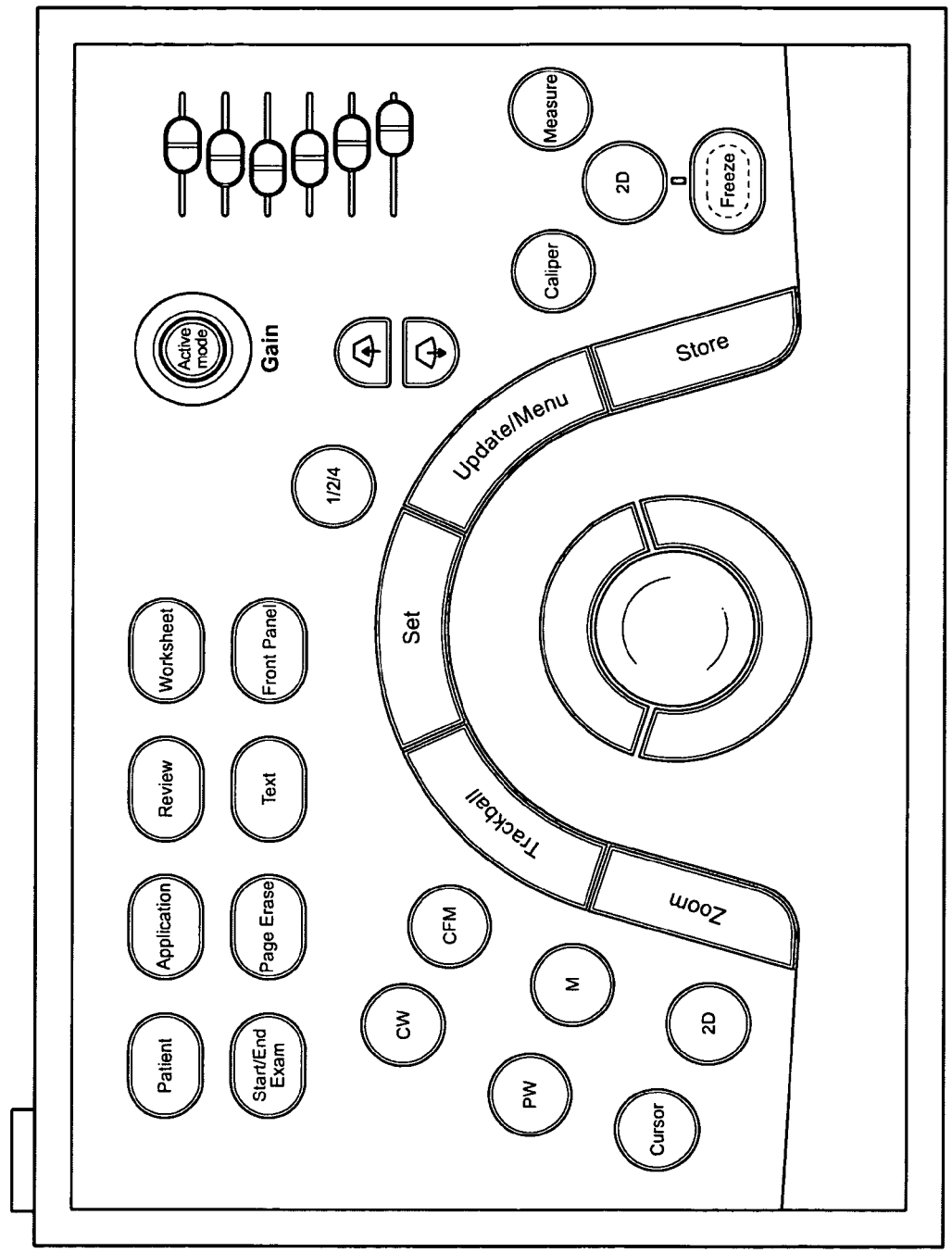
FIG. 15 illustrates a keyboard that provides all or essentially all of the keys that are present on an ultrasound system.

In all of the above configurations, keyboard 910 can be a keyboard that provides all or essentially all of the keys that are present on ultrasound system 308. A keyboard that has such keys is illustrated in FIG. 15. The use of such a keyboard (in configurations that do not exclude physical keyboard control of ultrasound system 308) allow all or essentially all of the functions of ultrasound system 308 to be performed remotely by the same keypress or keypresses that would be performed locally. However, keyboard 910 can replaced with a standard PC keyboard 930 if the necessary ultrasound control functions are mapped to the available keys on PC keyboard 930. Other types of keyboards may also be used with appropriate mappings.

Unless otherwise explicitly excluded, in configurations in which a keyboard is used, a mouse or other suitable pointing device and/or a voice recognition module and microphone may also be provided in conjunction with, or in appropriate cases, instead of the keyboard.

The term "co-displays" is not limited to displaying information on a common CRT or monitor, but instead refers also to the use of multiple monitors located in immediately adjacent one another to facilitate substantially simultaneous viewing by a single individual.

The figures illustrate diagrams of the functional blocks of various. The functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like). Similarly, the programs may be stand alone programs, may be incorporated as subroutines in an operating system, may be functions in an installed imaging software package, and the like.

While the invention has been described in terms of various specific embodiments, those skilled in the art will recognize that the invention can be practiced with modification within the spirit and scope of the claims.

What is claimed is:

1. A physiology workstation, comprising:
a communications interface conveying intracardiac (IC) physiology signals derived from a region of interest of a subject and ultrasound data representative of the region of interest of the subject, the IC physiology signals being produced by at least one of an IC electrophysiology (EP) catheter and a hemodynamic (HD) catheter within a heart of a subject during at least one of an EP and HD procedure, the ultrasound data being obtained by an ultrasound device in real-time during the at least one of an EP and HD procedure carried out on the subject;
a physiology processing unit receiving and processing the IC physiology signals during at least one of an EP and HD procedure;
an ultrasound processing unit receiving and processing the ultrasound data to generate ultrasound images, the physiology processing unit combining the IC physiology signals with the ultrasound images from the ultrasound processing unit; and
a display unit displaying the IC physiology signals and the ultrasound images, the IC physiology signals and ultrasound signals being presented jointly to a user in real-time during the at least one of an EP and HD procedure being carried out on the subject;
wherein the display unit includes at least one monitor, the monitor co-displaying the IC physiology signals and ultrasound images in adjacent windows on a single display; and
wherein the physiology processing unit, ultrasound processing unit and display unit are located in a control room that is divided from a procedure room where the subject is located, the communications interface extending between the procedure and control rooms and the physiology processing unit configured to remotely control the ultrasound device via said communications interface.

2. The workstation of claim 1, wherein the display unit includes at least one monitor that simultaneously displays the IC physiology signals in real-time, previously acquired IC physiology signals acquired from a memory device, ultrasound images in real-time, and images acquired from at least one of a MR, CT, ultrasound, PET, NM and X-ray system.

3. The workstation of claim 1, further comprising an ultrasound device having at least one of an intracardiac electrophysiology catheter, a handheld probe, an intravascular ultrasound catheter, an intraoperative probe, and a transesophageal probe.

4. The workstation of claim 1, further comprising an ultrasound device having an intravascular ultrasound catheter.

5. The workstation of claim 1, further comprising an ultrasound device including a scan converter module, the ultrasound device located remote from the ultrasound processor unit, the scan converter module operating upon ultrasound signals received from the ultrasound device to form ultrasound images, the ultrasound images including at least one of color flow, power Doppler, B-mode, spectral Doppler, 3-D or 4-D reconstruction of 2-D obtained images, ARFI and M-Mode information, the scan converter module conveying the ultrasound images over the communications interface to the ultrasound processor unit.

6. The workstation of claim 1, further comprising an ultrasound device coupled to a scan converter module, the ultrasound device located remote from the ultrasound processor unit, the scan converter module operating upon ultrasound signals received from the ultrasound device to form ultrasound images, the ultrasound images including 3-D or 4-D reconstruction of 2-D obtained images, the scan converter module conveying the ultrasound images over the communications interface to the ultrasound processor unit.

7. The workstation of claim 1, wherein the ultrasound processor unit comprises a mid-processor that receives complex data pairs as the ultrasound data over the communications interface, the mid-processor operating upon the data pairs to form vector data values associated with ultrasound images, the mid-processor processing the data pairs based on at least one of color flow, power Doppler, B-mode, spectral Doppler, 3-D or 4-D reconstruction of 2-D obtained images, ARFI and M-Mode operations to form the vector data values.

8. The workstation of claim 1, wherein the ultrasound processor unit comprises a scan converter module that receives vector data values as the ultrasound data over the communications interface, the scan converter operating upon the vector data values to form ultrasound images, the ultrasound images including 3-D or 4-D reconstruction of 2-D obtained images.

9. The workstation of claim 1, further comprising memory storing non-ultrasound and ultrasound images each having a time stamp identifying when the non-ultrasound and ultrasound images were obtained with respect to an EGG, the physiology processing unit generating the time stamps.

10. The workstation of claim 1, further comprising an EP catheter and stimulator, the physiology control module communicating with the stimulator to cause delivery of at least one of pacing and defibrillating signals within the heart during an EP procedure.

11. The workstation of claim 1, further comprising a mapping device that communicates with catheter position sensors to monitor a position of the at least one of an EP catheter and an HD catheter within the heart.

12. The workstation of claim 1, wherein the image frames illustrate a region of interest in the heart and a position and placement within the heart of the at least one of an EP catheter and an HD catheter.

13. The workstation of claim 1, further comprising an intravascular ultrasound (IVUS) system joined to an ultrasound catheter provided within the heart, the IVUS system providing the ultrasound data to the ultrasound processing unit.

14. A physiology workstation, comprising:
    an ultrasound device having an intravascular ultrasound catheter;
    a communications interface conveying intracardiac (IC) physiology signals derived from a subject and ultrasound data representative of a region of interest of the subject, the IC physiology signals being produced by at least one of an IC electrophysiology (EP) catheter and a hemodynamic (HD) catheter within a heart of a subject during at least one of an EP and HD procedure, the ultrasound data being obtained by the ultrasound device in real-time during the at least one of an EP and HD procedure carried out on the subject;
    a physiology processing unit receiving and processing the IC physiology signals;
    an ultrasound processing unit receiving and processing the ultrasound data to generate ultrasound images, the physiology processing unit combining the IC physiology signals with the ultrasound images from the ultrasound processing unit; and
    a display unit displaying the IC physiology signals and the ultrasound images, the IC physiology signals and ultrasound signals being presented jointly to a user in real-time during the at least one of an EP and HD procedure being carried out on the subject; and
    wherein the display unit includes at least one monitor, the monitor co-displaying the IC physiology signals and ultrasound images in adjacent windows on a single display.

15. The workstation of claim 14, wherein the ultrasound device includes a scan converter module, the ultrasound device located remote from the ultrasound processor unit, the scan converter module operating upon ultrasound signals received from the ultrasound device to form ultrasound images, the ultrasound images including 3-D or 4-D reconstruction of 2-D obtained images, the scan converter module conveying the ultrasound images over the communications interface to the ultrasound processor unit.

16. The workstation of claim 14, wherein the ultrasound processor unit comprises a scan converter module, the scan converter operating upon vector data values to form ultrasound images, the ultrasound images including 3-D or 4-D reconstruction of 2-D obtained images.

* * * * *

UNITED STATES PATENT AND TRADEMARK OFFICE
CERTIFICATE OF CORRECTION

| | | |
|---|---|---|
| PATENT NO. | : 7,572,223 B2 | Page 1 of 1 |
| APPLICATION NO. | : 11/433951 | |
| DATED | : August 11, 2009 | |
| INVENTOR(S) | : Brenda Donaldson | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 386 days.

Signed and Sealed this

Seventh Day of September, 2010

David J. Kappos
*Director of the United States Patent and Trademark Office*